(12) United States Patent
Marquis, Jr. et al.

(10) Patent No.: US 7,902,394 B2
(45) Date of Patent: Mar. 8, 2011

(54) CALCILYTIC COMPOUNDS

(75) Inventors: Robert W. Marquis, Jr., Collegeville, PA (US); Joshi M. Ramanjulu, Collegeville, PA (US); Robert Trout, Collegeville, PA (US)

(73) Assignee: GlaxoSmithKline LLC, Philadelphia, PA (US)

( * ) Notice: Subject to any disclaimer, the term of this patent is extended or adjusted under 35 U.S.C. 154(b) by 85 days.

(21) Appl. No.: 12/518,482

(22) PCT Filed: Dec. 18, 2007

(86) PCT No.: PCT/US2007/087866
§ 371 (c)(1),
(2), (4) Date: Jun. 10, 2009

(87) PCT Pub. No.: WO2008/077009
PCT Pub. Date: Jun. 26, 2008

(65) Prior Publication Data
US 2010/0029782 A1    Feb. 4, 2010

Related U.S. Application Data

(60) Provisional application No. 60/870,432, filed on Dec. 18, 2006.

(51) Int. Cl.
*C07C 229/00* (2006.01)
*C07D 333/12* (2006.01)
*A01N 37/10* (2006.01)

(52) U.S. Cl. ............. 560/39; 562/442; 549/74; 524/532

(58) Field of Classification Search .................. None
See application file for complete search history.

(56) References Cited

U.S. PATENT DOCUMENTS

| 6,291,459 B1 | 9/2001 | Bhatnager et al. | 514/237.8 |
| 7,514,473 B2 * | 4/2009 | Marquis et al. | 514/567 |

FOREIGN PATENT DOCUMENTS

| WO | WO 01/08673 A1 | 2/2001 |
| WO | WO 2004/047751 A2 | 6/2004 |
| WO | WO 2005/108373 A1 | 11/2005 |

OTHER PUBLICATIONS

Pandey et al., ARKIVOC, vol. XIV, pp. 10-14 (2006).

* cited by examiner

*Primary Examiner* — Karl J Puttlitz
(74) *Attorney, Agent, or Firm* — Duke M. Fitch; Kathryn L. Sieburth; Lorraine Ling

(57) ABSTRACT

Novel calcilytic compounds of Formula (I), pharmaceutical compositions, methods of synthesis, and methods of using them are provided.

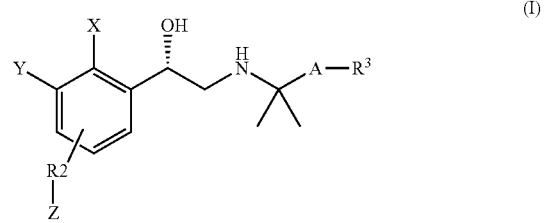

17 Claims, No Drawings

CALCILYTIC COMPOUNDS

This application is a 371 of International Application No. PCT/US2007/087866, filed Dec. 18, 2007, which claims the benefit of U.S. Provisional Application No. 60/870,432, filed Dec. 18, 2006, which are incorporated herein in their entireties.

FIELD OF INVENTION

The present invention relates to novel calcilytic compounds, pharmaceutical compositions containing these compounds, processes for their preparation and their use as calcium receptor antagonists.

BACKGROUND OF THE INVENTION

In mammals, extracellular $Ca^{2+}$ is under rigid homeostatic control and regulates various processes such as blood clotting, nerve and muscle excitability, and proper bone formation. Extracellular $Ca^{2+}$ inhibits the secretion of parathyroid hormone ("PTH") from parathyroid cells, inhibits bone resorption by osteoclasts, and stimulates secretion of calcitonin from C-cells. Calcium receptor proteins enable certain specialized cells to respond to changes in extracellular $Ca^{2+}$ concentration.

PTH is the principal endocrine factor regulating $Ca^{2+}$ homeostasis in the blood and extracellular fluids. PTH, by acting on bone and kidney cells, increases the level of $Ca^{2+}$ in the blood. This increase in extracellular $Ca^{2+}$ then acts as a negative feedback signal, depressing PTH secretion. The reciprocal relationship between extracellular $Ca^{2+}$ and PTH secretion forms an important mechanism maintaining bodily $Ca^{2+}$ homeostasis.

Extracellular $Ca^{2+}$ acts directly on parathyroid cells to regulate PTH secretion. The existence of a parathyroid cell surface protein which detects changes in extracellular $Ca^{2+}$ has been confirmed. See Brown et al., Nature 366:574, 1993. In parathyroid cells, this protein, the calcium receptor, acts as a receptor for extracellular $Ca^{2+}$, detects changes in the ion concentration of extracellular $Ca^{2+}$, and initiates a functional cellular response, PTH secretion.

Extracellular $Ca^{2+}$ influences various cell functions, reviewed in Nemeth et al., Cell Calcium 11:319, 1990. For example, extracellular $Ca^{2+}$ plays a role in parafollicular (C-cells) and parathyroid cells. See Nemeth, Cell Calcium 11:323, 1990. The role of extracellular $Ca^{2+}$ on bone osteoclasts has also been studied. See Zaidi, Bioscience Reports 10:493, 1990.

Various compounds are known to mimic the effects of extra-cellular $Ca^{2+}$ on a calcium receptor molecule. Calcilytics are compounds able to inhibit calcium receptor activity, thereby causing a decrease in one or more calcium receptor activities evoked by extracellular $Ca^{2+}$. Calcilytics are useful as lead molecules in the discovery, development, design, modification and/or construction of useful calcium modulators, which are active at $Ca^{2+}$ receptors. Such calcilytics are useful in the treatment of various disease states characterized by abnormal levels of one or more components, e.g., polypeptides such as hormones, enzymes or growth factors, the expression and/or secretion of which is regulated or affected by activity at one or more $Ca^{2+}$ receptors. Target diseases or disorders for calcilytic compounds include diseases involving abnormal bone and mineral homeostasis.

Abnormal calcium homeostasis is characterized by one or more of the following activities: an abnormal increase or decrease in serum calcium; an abnormal increase or decrease in urinary excretion of calcium; an abnormal increase or decrease in bone calcium levels (for example, as assessed by bone mineral density measurements); an abnormal absorption of dietary calcium; an abnormal increase or decrease in the production and/or release of messengers which affect serum calcium levels such as PTH and calcitonin; and an abnormal change in the response elicited by messengers which affect serum calcium levels.

Thus, calcium receptor antagonists offer a unique approach towards the pharmacotherapy of diseases associated with abnormal bone or mineral homeostasis, such as hypoparathyroidism, osteosarcoma, periodontal disease, fracture healing, osteoarthritis, rheumatoid arthritis, Paget's disease, humoral hypercalcemia associated with malignancy and fracture healing, and osteoporosis.

SUMMARY OF THE INVENTION

The present invention relates to calcium receptor antagonists represented by compounds of Formula (I), as indicated hereinbelow, compositions comprising the present compounds, and their use as calcium receptor antagonists in the treatment of a variety of diseases associated with abnormal bone or mineral homeostasis, including but not limited to, hypoparathyroidism, osteosarcoma, periodontal disease, fracture healing, osteoarthritis, rheumatoid arthritis, Paget's disease, humoral hypercalcemia associated with malignancy and fracture healing, and osteoporosis.

The present invention further provides a method for antagonizing calcium receptors in an animal, including humans, which comprises administering to an animal in need thereof an effective amount of a compound of Formula (I), as indicated hereinbelow.

The present invention further provides a method for increasing serum parathyroid levels in an animal, including humans, which comprises administering to an animal in need thereof an effective amount of a compound of Formula (I) as indicated hereinbelow.

The present invention further provides methods for preparing compounds of Formula (I), as indicated hereinbelow.

DETAILED DESCRIPTION OF THE INVENTION

The present invention relates to novel compounds according to Formula (I):

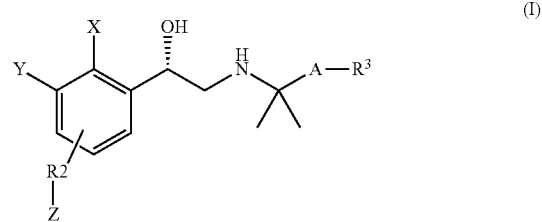

wherein:
X is halogen;
Y is hydrogen or halogen;
Z is —C(O)OH or —C(O)OC$_{1-5}$alkyl;
R2 is a covalent bond or C$_{1-5}$alkyl;
R3 is phenyl, thienyl, naphthyl or dihydroindenyl, wherein the thienyl and phenyl moieties are optionally substituted, independently, once or twice, by halogen, C$_{1-5}$alkyl, C$_{1-5}$alkoxy or C$_{1-5}$alkylthio; and
A is a covalent bond or C$_{1-5}$alkyl;
or a pharmaceutically acceptable salt thereof.

As used herein, "$C_{1-5}$alkyl" refers to a linear or branched saturated hydrocarbon group containing 1 to 5 carbon atoms. Examples of such groups include methyl, ethyl, n-propyl, isopropyl, n-butyl, isobutyl, sec-butyl, tert butyl, n-pentyl, isopentyl, sec-pentyl and tert pentyl.

As used herein, "$C_{1-5}$alkoxy" refers to an —O—$C_{1-5}$alkyl group wherein $C_{1-5}$alkyl is as defined herein. Examples of such groups include methoxy, ethoxy, propoxy, butoxy and pentoxy.

As used herein "$C_{1-5}$alkylthio" refers to a —S—$C_{1-5}$alkyl group wherein $C_{1-5}$alkyl is as defined herein. Examples include methylthio, ethylthio, propylthio, butylthio and pentylthio.

As used herein, "halogen" refers to F, Cl, Br or I.

In one embodiment, the —R2-Z moiety is in the meta or para position on the phenyl ring relative to the amino alcohol side chain.

In one embodiment, the —R2-Z moiety is in the meta position on the phenyl ring relative to the amino alcohol side chain.

Suitably, X is halogen.
In one embodiment, X is Cl, F, or Br.
In another embodiment, X is Cl or F.
In another embodiment, X is F.
Suitably, Y is hydrogen or halogen.
In one embodiment, Y is hydrogen.
In another embodiment, Y is halogen.
In another embodiment, Y is F or Cl
In another embodiment, Y is F.
Suitably, Z is —C(O)OH or —C(O)O$C_{1-5}$alkyl.
In one embodiment, Z is —C(O)OH.
In another embodiment, Z is —C(O)O$C_{1-5}$alkyl.
In another embodiment, Z is —C(O)Omethyl or —C(O)Oethyl.
In another embodiment, Z is —C(O)Oethyl.
Suitably, R2 is a covalent bond or $C_{1-5}$alkyl.
In one embodiment, R2 is a covalent bond.
In another embodiment, R2 is $C_{1-5}$alkyl.
In another embodiment, R2 is ethyl, propyl, or butyl.
In another embodiment, R2 is ethyl.
Suitably, R3 is phenyl, thienyl, naphthyl, or dihydroindenyl, wherein the thienyl and phenyl moieties are optionally substituted, independently, once or twice, by halogen, $C_{1-5}$alkyl, $C_{1-5}$alkoxy or $C_{1-5}$alkylthio.
In one embodiment, R3 is naphthyl.
In another embodiment, R3 is dihydroindenyl.
In another embodiment, R3 is 2,3-dihydro-1H-inden-2-yl.
In another embodiment, R3 is thienyl, optionally substituted once by $C_{1-4}$alkyl or halogen.
In another embodiment, R3 is thienyl, optionally substituted by Cl.
In another embodiment, R3 is 5-chloro-2-thienyl.
In another embodiment, R3 is thienyl, optionally substituted by methyl.
In another embodiment, R3 is 5-methyl-2-thienyl.
In another embodiment R3 is thienyl.
In one embodiment, R3 is phenyl, optionally substituted, independently, once or twice, by halogen, $C_{1-5}$alkyl, $C_{1-5}$alkoxy or $C_{1-5}$alkylthio.
In one embodiment, R3 is phenyl.
In another embodiment, R3 is phenyl, substituted once by halogen, $C_{1-5}$alkyl, $C_{1-5}$alkoxy or $C_{1-5}$alkylthio.
In another embodiment, R3 is phenyl, substituted once by Br, methoxy, methylthio, or tert butyl.
In another embodiment, R3 is phenyl, substituted independently, twice, by halogen or $C_{1-5}$alkyl.
In another embodiment, R3 is 4-chloro-3-fluorophenyl.
In another embodiment, R3 is 4-chloro-2-fluorophenyl.
In another embodiment, R3 is 3-fluoro-4-methylphenyl.
Suitably, A is a covalent bond or $C_{1-5}$alkyl.
In one embodiment, A is a covalent bond.
In another embodiment, A is $C_{1-5}$alkyl.
In another embodiment, A is methyl, ethyl or propyl.
In one embodiment, A is propyl.
In another embodiment, A is methyl.

Illustrative compounds of the present invention include, but are not limited to:

3-(3-{(1S)2-[(1,1-dimethyl-4-phenylbutyl)amino]-1-hydroxyethyl}-4,5-difluorophenyl)propanoic acid;

ethyl 3-(3-{(1S)-2-[(1,1-dimethyl-4-phenylbutyl)amino]-1-hydroxyethyl}-4,5-difluorophenyl)propanoate;

ethyl 3-[3-((1S)-2-{[2-(2,3-dihydro-1H-inden-2-yl)-1,1-dimethylethyl]amino}-1-hydroxyethyl)-4,5-difluorophenyl]propanoate;

3-[3-((1S)-2-{[2-(2,3-dihydro-1H-inden-2-yl)-1,1-dimethylethyl]amino}-1-hydroxyethyl)-4,5-difluorophenyl]propanoic acid;

5-(3-{(1S)-2-[(1,1-dimethyl-4-phenyl butyl)amino]-1-hydroxyethyl}-4,5-difluorophenyl)pentanoic acid;

5-[3-((1S)-2-{[2-(2,3-dihydro-1H-inden-2-yl)-1,1-dimethylethyl]amino}-1-hydroxyethyl)-4,5-difluorophenyl]pentanoic acid;

4-(3-{(1S)-2-[(1,1-dimethyl-4-phenylbutyl)amino]-1-hydroxyethyl}-4,5-difluorophenyl)butanoic acid;

4-[3-((1S)-2-{[2-(2,3-dihydro-1H-inden-2-yl)-1,1-dimethylethyl]amino}-1-hydroxyethyl)-4,5-difluorophenyl]butanoic acid;

3-(3-{(1S)-2-[(1,1-dimethyl-5-phenyl pentyl)amino]-1-hydroxyethyl}-4,5-difluorophenyl)propanoic acid;

3-(3-{2-[(1,1-dimethyl-6-phenylhexyl)amino]-1-hydroxyethyl}-4,5-difluorophenyl)propanoic acid;

3-[3-((1S)-2-{[2-(4-chloro-3-fluorophenyl)-1,1-dimethylethyl]amino}-1-hydroxyethyl)-4,5-difluorophenyl]propanoic acid;

3-{3-[(1S)-2-({1,1-dimethyl-2-[4-(methyloxy)phenyl]ethyl}amino)-1-hydroxyethyl]-4,5-difluorophenyl}propanoic acid;

3-[3-((1S)-2-{[1,1-dimethyl-2-(2-naphthalenyl)ethyl]amino}-1-hydroxyethyl)-4,5-difluorophenyl]propanoic acid;

3-(3-{(1S)-2-[(1,1-dimethyl-2-phenylethyl)amino]-1-hydroxyethyl}-4,5-difluorophenyl)propanoic acid;

3-(3,4-difluoro-5-{(1S)-1-hydroxy-2-[(1-methyl-1-phenylethyl)amino]ethyl}phenyl)propanoic acid;

3-[3-((1S)-2-{[2-(4-chloro-2-fluorophenyl)-1,1-dimethylethyl]amino}-1-hydroxyethyl)-4,5-difluorophenyl]propanoic acid;

3-[3-((1S)-2-{[1,1-dimethyl-2-(5-methyl-2-thienyl)ethyl]amino}-1-hydroxyethyl)-4,5-difluorophenyl]propanoic acid;

3-{3-[(1S)-2-({1,1-dimethyl-3-[4-(methyloxy)phenyl]propyl}amino)-1-hydroxyethyl]-4,5-difluorophenyl}propanoic acid;

3-[3,4-difluoro-5-((1S)-2-{[2-(3-fluoro-4-methylphenyl)-1,1-dimethylethyl]amino}-1-hydroxyethyl)phenyl]propanoic acid;

3-{3-[(1S)-2-({1,1-dimethyl-2-[4-(methylthio)phenyl]ethyl}amino)-1-hydroxyethyl]-4,5-difluorophenyl}propanoic acid;

3-{3-[(1S)-2-({2-[4-(1,1-dimethylethyl)phenyl]-1,1-dimethylethyl}amino)-1-hydroxyethyl]-4,5-difluorophenyl}propanoic acid;

3-[3-((1S)-2-{[1,1-dimethyl-2-(2-thienyl)ethyl]amino}-1-hydroxyethyl)-4,5-difluorophenyl]propanoic acid;

3-(3-{(1S)-2-[(1,1-dimethyl-3-phenylpropyl)amino]-1-hydroxyethyl}-4,5-difluorophenyl)propanoic acid;
3-[3-((1S)-2-{[2-(4-bromophenyl)-1,1-dimethylethyl]amino}-1-hydroxyethyl)-4,5-difluorophenyl]propanoic acid;
3-[3-((1S)-2-{[2-(5-chloro-2-thienyl)-1,1-dimethylethyl]amino}-1-hydroxyethyl)-4,5-difluorophenyl]propanoic acid;
2-(3-{(1S)-2-[(1,1-dimethyl-4-phenylbutyl)amino]-1-hydroxyethyl}-4,5-difluorophenyl)-2-methylpropanoic acid;
2-[3-((1S)-2-{[2-(2,3-dihydro-1H-inden-2-yl)-1,1-dimethylethyl]amino}-1-hydroxyethyl)-4,5-difluorophenyl]-2-methylpropanoic acid;
3-(4-chloro-3-{(1S)-2-[(1,1-dimethyl-4-phenylbutyl)amino]-1-hydroxyethyl}phenyl)propanoic acid;
3-(4-bromo-3-{2-[(1,1-dimethyl-4-phenylbutyl)amino]-1-hydroxyethyl}phenyl)propanoic acid;
3-[4-bromo-3-(2-{[2-(2,3-dihydro-1H-inden-2-yl)-1,1-dimethylethyl]amino}-1-hydroxyethyl)phenyl]propanoic acid;
3-(2,3-dichloro-4-{(1S)-2-[(1,1-dimethyl-4-phenylbutyl)amino]-1-hydroxyethyl}phenyl)propanoic acid;
5-[2,3-dichloro-4-((1S)-2-{[2-(2,3-dihydro-1H-inden-2-yl)-1,1-dimethylethyl]amino}-1-hydroxyethyl)phenyl]pentanoic acid;
3-{2-[(1,1-dimethyl-4-phenylbutyl)amino]-1-hydroxyethyl}-4,5-difluorobenzoic acid;
3-(2-{[2-(2,3-dihydro-1H-inden-2-yl)-1,1-dimethylethyl]amino}-1-hydroxyethyl)-4,5-difluorobenzoic acid;
3-(3-{(1S)-2-[(1,1-dimethyl-4-phenylbutyl)amino]-1-hydroxyethyl}-4,5-difluorophenyl)-2,2-dimethylpropanoic acid; and
3-[3-((1S)-2-{[2-(2,3-dihydro-1H-inden-2-yl)-1,1-dimethylethyl]amino}-1-hydroxyethyl)-4,5-difluorophenyl]-2,2-dimethylpropanoic acid;
or a pharmaceutically acceptable salt thereof.

As used herein, the term "pharmaceutically acceptable" means a compound which is suitable for pharmaceutical use. Salts of compounds of the invention which are suitable for use in medicine are those wherein the counterion is pharmaceutically acceptable.

Compounds of the invention may contain one or more asymmetric carbon atoms and may occur as racemates, diastereomers, individual enantiomers and resolved diastereomers. All of these forms are contemplated to be within the scope of the present invention, including mixtures thereof.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compounds of the invention, including pharmaceutically acceptable solvates, are within the scope of the invention.

Furthermore, some of the crystalline forms of the compounds of Formula (I) may exist as polymorphs. Polymorphs of the compounds of the invention are within the scope of the invention.

Because of their potential use in medicine, the salts of the compounds of Formula (I) are pharmaceutically acceptable. Suitable pharmaceutically acceptable salts can include acid or base addition salts.

A pharmaceutically acceptable acid addition salt may be formed by reaction of a compound of Formula (I) with a suitable inorganic or organic acid (such as hydrobromic, hydrochloric, sulfuric, nitric, phosphoric, succinic, maleic, formic, acetic, propionic, fumaric, citric, tartaric, lactic, benzoic, salicylic, glutamic, aspartic, p-toluenesulfonic, benzenesulfonic, methanesulfonic, ethanesulfonic, naphthalenesulfonic such as 2-naphthalenesulfonic, or hexanoic acid), optionally in a suitable solvent such as an organic solvent, to give the salt which is usually isolated for example by crystallisation and filtration. A pharmaceutically acceptable acid addition salt of a compound of Formula (I) may comprise or be for example a hydrobromide, hydrochloride, sulfate, nitrate, phosphate, succinate, maleate, formate, acetate, propionate, fumarate, citrate, tartrate, lactate, benzoate, salicylate, glutamate, aspartate, p-toluenesulfonate, benzenesulfonate, methanesulfonate, ethanesulfonate, naphthalenesulfonate (e.g. 2-naphthalenesulfonate) or hexanoate salt.

A pharmaceutically acceptable base addition salt may be formed by reaction of a compound of Formula (I) with a suitable organic base (e.g. triethylamine, ethanolamine, triethanolamine, choline, arginine, lysine or histidine), optionally in a suitable solvent such as an organic solvent, to give the base addition salt which is usually isolated for example by crystallisation and filtration. Other suitable pharmaceutically acceptable salts include pharmaceutically acceptable metal salts, for example pharmaceutically acceptable alkali-metal or alkaline-earth-metal salts such as sodium, potassium, calcium or magnesium salts.

The invention includes within its scope all possible stoichiometric and non-stoichiometric forms of the salts of the compounds of Formula (I).

Synthetic Schemes:

The present compounds may be synthesized according to a process comprising the steps of:

(a) selective tosylation of a diol according to Formula (II):

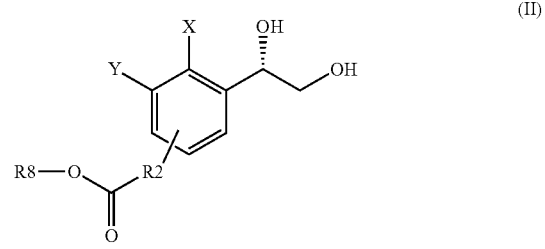

wherein R8 is $C_{1-5}$alkyl, and X, Y and R2 are as defined in Formula (I);

to yield a tosylate according to Formula (III):

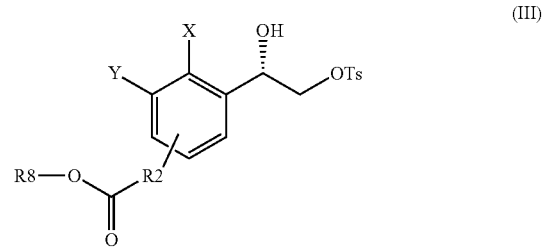

(b) reaction of the tosylate with a base to provide an epoxide according to Formula (IV):

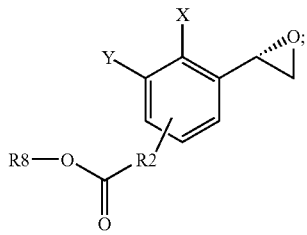
(IV)

and (c) opening of the epoxide with a primary amine to provide an amino alcohol according to Formula (V):

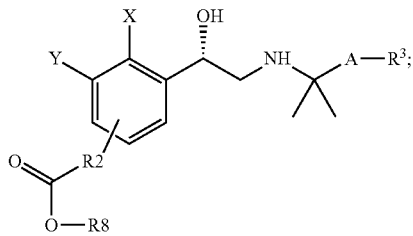
(V)

wherein R3 is as defined in Formula (I).

The compound according to Formula (V) may also be hydrolysed to generate an acid according to Formula (VI):

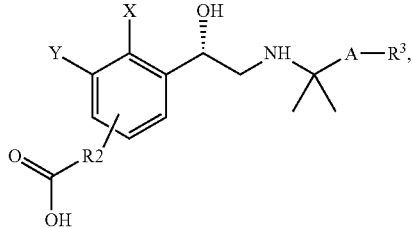
(VI)

wherein X, Y, R2, A and R3 are as defined in Formula (I).

Intermediates involved in the present invention are represented by Formulas (II), (III) and (IV):

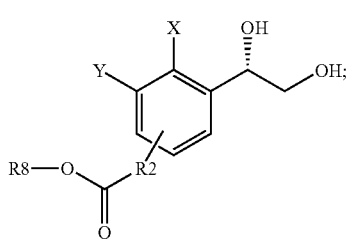
(II)

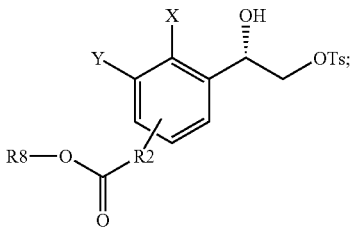
(III)

(IV)

wherein R8 is $C_{1-5}$alkyl and X, Y and R2 are as defined in Formula (I).

General synthetic methods are detailed below in Schemes 1-2 below. The present schemes are intended to be illustrative of the present invention and not limiting in any way. While particular substituents are disclosed, other variables can be made with the present schemes.

Scheme 1

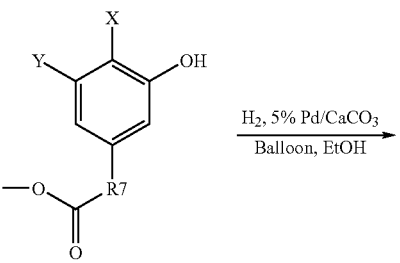

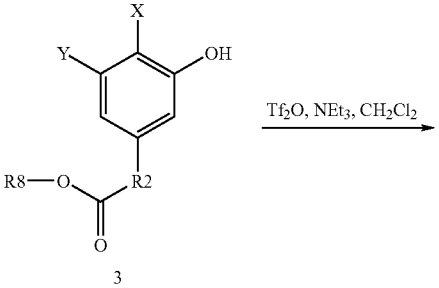

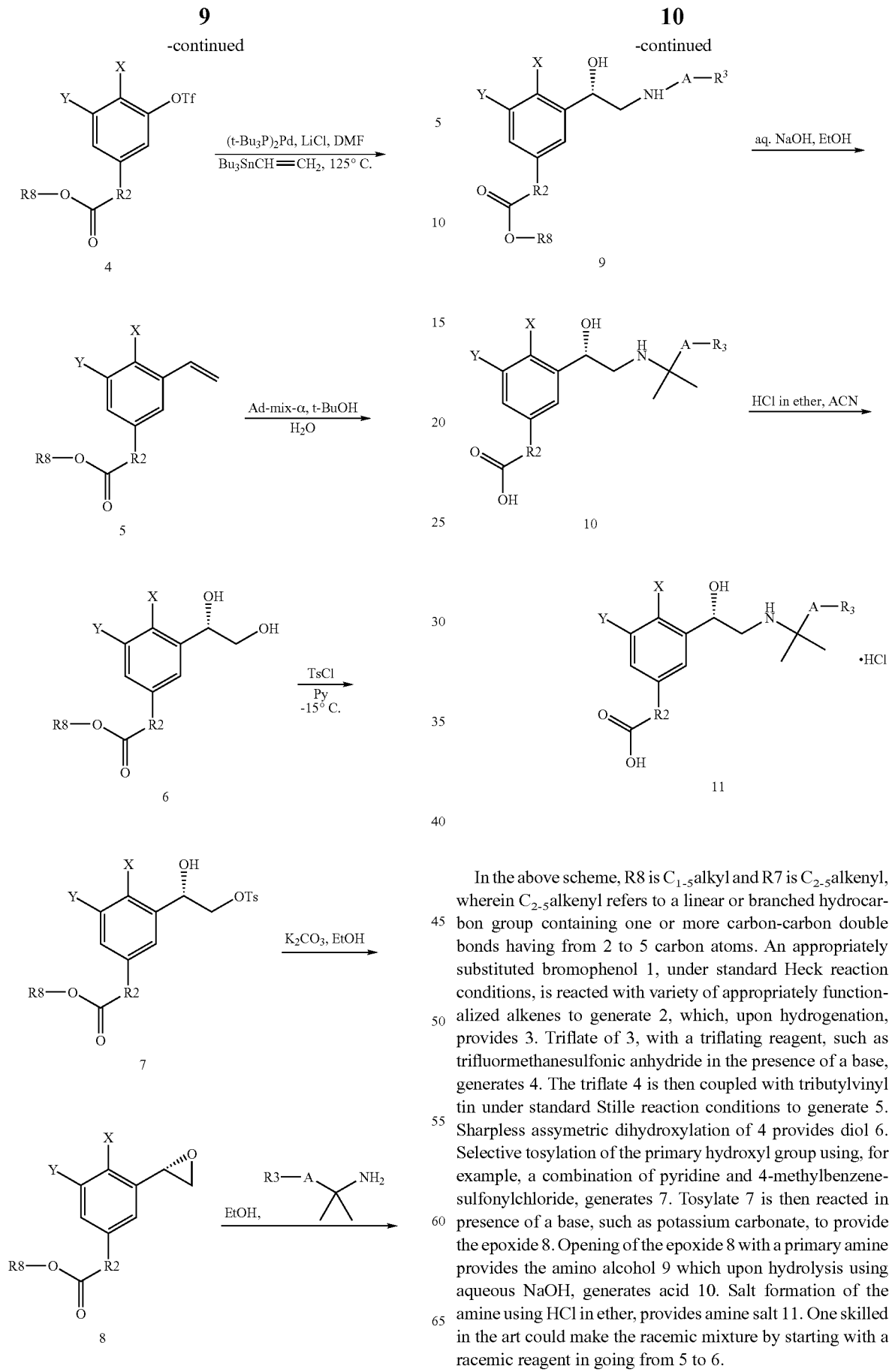

In the above scheme, R8 is $C_{1-5}$alkyl and R7 is $C_{2-5}$alkenyl, wherein $C_{2-5}$alkenyl refers to a linear or branched hydrocarbon group containing one or more carbon-carbon double bonds having from 2 to 5 carbon atoms. An appropriately substituted bromophenol 1, under standard Heck reaction conditions, is reacted with variety of appropriately functionalized alkenes to generate 2, which, upon hydrogenation, provides 3. Triflate of 3, with a triflating reagent, such as trifluormethanesulfonic anhydride in the presence of a base, generates 4. The triflate 4 is then coupled with tributylvinyl tin under standard Stille reaction conditions to generate 5. Sharpless assymetric dihydroxylation of 4 provides diol 6. Selective tosylation of the primary hydroxyl group using, for example, a combination of pyridine and 4-methylbenzenesulfonylchloride, generates 7. Tosylate 7 is then reacted in presence of a base, such as potassium carbonate, to provide the epoxide 8. Opening of the epoxide 8 with a primary amine provides the amino alcohol 9 which upon hydrolysis using aqueous NaOH, generates acid 10. Salt formation of the amine using HCl in ether, provides amine salt 11. One skilled in the art could make the racemic mixture by starting with a racemic reagent in going from 5 to 6.

Scheme 2

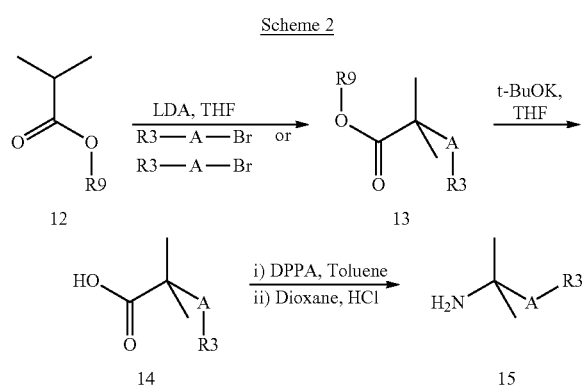

Scheme 2 shows the preparation of the primary amine used in Scheme 1. In the above scheme, R9 represents $C_{1-5}$alkyl. Alkylation of iso-butyrate ester 12 with an alkylating agent in the presence of a base such as lithium N,N-diisopropyl amide, provides 13. The ester 13, upon hydrolysis using t-BuOK in THF and water, generates acid 14. Acid 14 can then be converted to amine salt 15 using standard Curtius rearrangement conditions followed by HCl salt formation with an appropriate solvent containing HCl.

In order to use a compound of Formula (I) or a pharmaceutically acceptable salt thereof for the treatment of humans and other mammals, it is normally formulated in accordance with standard pharmaceutical practice as a pharmaceutical composition.

The calcilytic compounds may be administered by different routes including intravenous, intraperitoneal, subcutaneous, intramuscular, oral, topical (e.g. transdermal), or transmucosal administration. For systemic administration, oral administration is preferred. For oral administration, for example, the compounds may be formulated into conventional oral dosage forms such as capsules, tablets, and liquid preparations such as syrups, elixirs, and concentrated drops.

Alternatively, injection (parenteral administration) may be used, e.g., for intramuscular, intravenous, intraperitoneal, and subcutaneous administration. For injection, the compounds of the invention are formulated in liquid solutions, preferably, in physiologically compatible buffers or solutions, such as saline solution, Hank's solution, or Ringer's solution. In addition, the compounds may be formulated in solid form and redissolved or suspended immediately prior to use. Lyophilized forms may also be produced. In one embodiment, the parenteral composition consists of a solution or suspension of a compound or salt in a sterile aqueous or non-aqueous carrier optionally containing a parenterally acceptable oil, for example polyethylene glycol, polyvinylpyrrolidone, lecithin, arachis oil or sesame oil.

Systemic administration may also be by transmucosal or transdermal means. For transmucosal or transdermal administration, penetrants appropriate to the barrier to be permeated are used in the formulation. Such penetrants are generally known in the art, and include, for example, for transmucosal administration, bile salts and fusidic acid derivatives. In addition, detergents may be used to facilitate permeation. Transmucosal administration, for example, may be through nasal sprays, rectal suppositories, or vaginal suppositories.

For topical administration, the compounds of the invention may be formulated into ointments, salves, gels, or creams, as is generally known in the art.

The amounts of various calcilytic compounds to be administered can be determined by standard procedures taking into account factors such as the compound $IC_{50}$, $EC_{50}$, the biological half-life of the compound, the age, size and weight of the patient, and the disease or disorder associated with the patient. Amounts administered also depend on the routes of administration and the degree of oral bioavailability. For example, for compounds with low oral bioavailability, relatively higher doses will have to be administered. The importance of these and other factors to be considered are known to those of ordinary skill in the art.

In one embodiment, the composition is in unit dosage form. For oral application, for example, a tablet, or capsule may be administered, for nasal application, a metered aerosol dose may be administered, for transdermal application, a topical formulation or patch may be administered and for transmucosal delivery, a buccal patch may be administered. In each case, dosing is such that the patient may administer a single dose.

Each dosage unit for oral administration contains suitably from 0.01 to 500 mg/Kg, and preferably from 0.1 to 50 mg/Kg, of a compound of Formula (I) or a pharmaceutically acceptable salt thereof, calculated as the free base. The daily dosage for parenteral, nasal, oral inhalation, transmucosal or transdermal routes contains suitably from 0.01 mg to 100 mg/Kg, of a compound of Formula (I), or pharmaceutically acceptable salt thereof. A topical formulation contains suitably 0.01 to 5.0% of a compound of Formula (I), or pharmaceutically acceptable salt thereof. The active ingredient may be administered, for example, from 1 to 6 times per day, such as, once, sufficient to exhibit the desired activity, as is readily apparent to one skilled in the art.

Compounds of Formula (I), and their pharmaceutically acceptable salts, which are active when given orally, can be formulated as syrups, tablets, capsules and lozenges. A syrup formulation will generally consist of a suspension or solution of the compound or salt in a liquid carrier for example, ethanol, peanut oil, olive oil, glycerine or water with a flavoring or coloring agent. Where the composition is in the form of a tablet, any pharmaceutical carrier routinely used for preparing solid formulations may be used. Examples of such carriers include magnesium stearate, terra alba, talc, gelatin, acacia, stearic acid, starch, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils, and are incorporated in a soft gelatin capsule shell.

Typical compositions for inhalation are in the form of a solution, suspension or emulsion that may be administered as a dry powder or in the form of an aerosol using a conventional propellant such as dichlorodifluoromethane or trichlorofluoromethane.

A typical suppository formulation comprises a compound of Formula (I) or a pharmaceutically acceptable salt thereof which is active when administered in this way, with a binding and/or lubricating agent, for example polymeric glycols, gelatins, cocoa-butter or other low melting vegetable waxes or fats or their synthetic analogs.

Typical dermal and transdermal formulations comprise a conventional aqueous or non-aqueous vehicle, for example a cream, ointment, lotion or paste or are in the form of a medicated plaster, patch or membrane.

In one embodiment, the composition is in unit dosage form, for example a tablet, capsule or metered aerosol dose, so that the patient may administer a single dose.

As used herein, "treatment" of a disease includes, but is not limited to, prevention, slowing the progression of and prophylaxis of the disease.

Diseases and disorders which might be treated (including prevented), based upon the affected cells, include bone and mineral-related diseases or disorders, (e.g. hypoparathyroidism), central nervous system disorders, seizures, stroke, head trauma, spinal cord injury, hypoxia-induced nerve cell damage (such as occurs in cardiac arrest or neonatal distress), epilepsy, neurodegenerative diseases (such as Alzheimer's disease, Huntington's disease and Parkinson's disease), dementia, muscle tension, depression, anxiety, panic disorder, obsessive-compulsive disorder, post-traumatic stress disorder, schizophrenia, neuroleptic malignant syndrome, and Tourette's syndrome. Diseases and disorders that might be treated also include diseases involving excess water reabsorption by the kidney, such as syndrome of inappropriate ADH secretion (SIADH), cirrhosis, congestive heart failure, nephrosis, hypertension, and renal toxicity from cationic antibiotics (e.g., aminoglycoside antibiotics). Gut motility disorders (such as diarrhea and spastic colon), GI ulcer diseases, GI diseases with excessive calcium absorption (such as sarcoidosis), might also be treated with the present compounds. Autoimmune diseases, organ transplant rejection, squamous cell carcinoma and pancreatitis might also be treated by the present compounds.

In one embodiment of the present invention, the present compounds are used to increase serum parathyroid hormone ("PTH") levels. Increasing serum PTH levels can be helpful in treating diseases such as hypoparathyroidism, osteosarcoma, periodontal disease, fracture, osteoarthritis, rheumatoid arthritis, Paget's disease, humoral hypercalcemia associated with malignancy and fracture healing, and osteoporosis.

Another aspect of the present invention describes a method of treating a patient comprising administering to the patient an amount of a present compound sufficient to increase the serum PTH level. In another embodiment, the method is carried out by administering an amount of the compound effective to cause an increase in duration and/or quantity of serum PTH level sufficient to have a therapeutic effect.

In various embodiments, the compound administered to a patient causes an increase in serum PTH having a duration of up to one hour, about one to about twenty-four hours, about one to about twelve hours, about one to about six hours, about one to about five hours, about one to about four hours, about two to about five hours, about two to about four hours, or about three to about six hours.

In an alternative embodiment of the present invention, the compound administered to a patient causes an increase in serum PTH having a duration of more than about twenty-four hours provided that it is co-administered with an anti-resorptive agent. As used herein, an "anti-resorptive agent" includes compounds that inhibit the resorption of bone by reducing bone turnover and erosion depth in subjects. Suitable anti-resorptive agents for co-administration include, but are not limited to estrogen, $1\alpha,25$-$(OH)_2D_3$, $1\alpha$-$(OH)D_3$, calcitonin, selective estrogen receptor modulators, vitronectin receptor antagonists, V-H+-ATPase inhibitors, src $SH_2$ antagonists, bisphosphonates and cathepsin K inhibitors.

In additional embodiments, the compound administered to a patient causes an increase in serum PTH of up to two fold, two to five fold, five to ten fold, or at least 10 fold, greater than baseline peak serum PTH in the patient. The baseline peak serum level is measured with respect to the patient before treatment.

The biological activity of the compounds of Formula (I), may be demonstrated by the following tests:
(I) Calcium Receptor Inhibitor Assay Calcilytic activity was measured by determining the $IC_{50}$ of the test compound for blocking increases of intracellular $Ca^{2+}$ elicited by extracellular $Ca^{2+}$ in HEK 293 4.0-7 cells stably expressing the human calcium receptor. HEK 293 4.0-7 cells were constructed as described by Rogers et al., *J. Bone Miner. Res.* 10 Suppl. 1:S483, 1995 (hereby incorporated by reference to the extent required to conduct the present assay). Intracellular $Ca^{2+}$ increases were elicited by increasing extracellular $Ca^{2+}$ from 1 to 1.75 mM. Intracellular $Ca^{2+}$ was measured using fluo-3, a fluorescent calcium indicator.

Cells were maintained in T-150 flasks in selection media (DMEM supplemented with 10% fetal bovine serum and 200 ug/mL hygromycin B), under 5% $CO_2$:95% air at 37° C. and were grown up to 90% confluency. The medium was decanted and the cell monolayer was washed twice with phosphate-buffered saline (PBS) kept at 37° C. After the second wash, 6 mL of 0.02% EDTA in PBS was added and incubated for 4 minutes at 37° C. Following the incubation, cells were dispersed by gentle agitation. Cells from 2 or 3 flasks were pooled and pelleted (100×g). The cellular pellet was resuspended in 10-15 mL of SPF-PCB+ and pelleted again by centrifugation. This washing was done twice.

Sulfate- and phosphate-free parathyroid cell buffer (SPF-PCB) contained 20 mM Na-Hepes, pH 7.4, 126 mM NaCl, 5 mM KCl, and 1 mM $MgCl_2$. SPF-PCB was made up and stored at 4° C. On the day of use, SPF-PCB was supplemented with 1 mg/mL of D-glucose and 1 mM $CaCl_2$ and then split into two fractions. To one fraction, bovine serum albumin (BSA; fraction V, ICN) was added at 5 mg/mL (SPF-PCB+). This buffer was used for washing, loading and maintaining the cells. The BSA-free fraction was used for diluting the cells in the cuvette for measurements of fluorescence.

The pellet was resuspended in 10 mL of SPF-PCB+ containing 2.2 uM fluo-3 (Molecular Probes) and incubated at room temperature for 35 minutes. Following the incubation period, the cells were pelleted by centrifugation. The resulting pellet was washed with SPF-PCB+. After this washing, cells were resuspended in SPF-PCB+ at a density of $1$-$2 \times 10^6$ cells/mL.

For recording fluorescent signals, 300 uL of cell suspension were diluted in 1.2 mL of SPF buffer containing 1 mM $CaCl_2$ and 1 mg/mL of D-glucose. Measurements of fluorescence were performed at 37° C. with constant stirring using a spectrofluorimeter. Excitation and emission wavelengths were measured at 485 and 535 nm, respectively. To calibrate fluorescence signals, digitonin (5 mg/mL in ethanol) was added to obtain Fmax, and the apparent Fmin was determined by adding Tris-EGTA (2.5 M Tris-Base, 0.3 M EGTA). The concentration of intracellular calcium was calculated using the following equation:

Intracellular calcium=$(F-F_{min}/F_{max}) \times K_d$; where $K_d$=400 nM.

To determine the potential calcilytic activity of test compounds, cells were incubated with test compound (or vehicle as a control) for 90 seconds before increasing the concentration of extracellular $Ca^{2+}$ from 1 to 2 mM. Calcilytic compounds were detected by their ability to block, in a concentration-dependent manner, increases in the concentration of intracellular $Ca^{2+}$ elicited by extracellular $Ca^{2+}$.

The present compounds were considered active at $IC_{50}$ values of lower than 10 uM. The present examples were all tested except for Examples 2, 3 and 26. The compounds testing active had an IC$_{50}$ value in a range of from about 50 nM to about 10 uM. Compounds in Examples 14, 16, 17, 18, 19, 20, 21, 22, 23 and 24 tested above 10 uM, which was the limit of the present assay.

(II) Calcium Receptor Binding Assay

HEK 293 4.0-7 cells stably transfected with the Human Parathyroid Calcium Receptor ("HuPCaR") were scaled up in T180 tissue culture flasks. Plasma membrane was obtained by polytron homogenization or glass douncing in buffer (50 mM Tris-HCl pH 7.4, 1 mM EDTA, 3 mM MgCl$_2$) in the presence of a protease inhibitor cocktail containing 1 uM Leupeptin, 0.04 uM Pepstatin, and 1 mM PMSF. Aliquoted membrane was snap frozen and stored at −80° C. $^3$H labeled compound was radiolabeled to a radiospecific activity of 44 Ci/mmole and was aliquoted and stored in liquid nitrogen for radiochemical stability.

A typical reaction mixture contained 2 nM $^3$H compound ((R,R)—N-4'-Methoxy-t-3-3'-methyl-1'-ethylphenyl-1-(1-naphthyl)ethylamine), or $^3$H compound (R)—N-[2-Hydroxy-3-(3-chloro-2-cyanophenoxy)propyl]-1,1-dimethyl-2-(4-methoxyphenyl)ethylamine with 4-10 ug membrane in homogenization buffer containing 0.1% gelatin and 10% EtOH in a reaction volume of 0.5 mL. Incubation was performed in 12×75 polyethylene tubes in an ice water bath. To each tube 25 uL of test sample in 100% EtOH was added, followed by 400 uL of cold incubation buffer, and 25 uL of 40 nM $^3$H-compound in 100% EtOH for a final concentration of 2 nM. The binding reaction was initiated by the addition of 50 uL of 80-200 ug/mL HEK 293 4.0-7 membrane diluted in incubation buffer, and allowed to incubate at 4° C. for 30 min. Wash buffer was 50 mM Tris-HCl containing 0.1% PEI. Nonspecific binding was determined by the addition of 100-fold excess of unlabeled homologous ligand, and was generally 20% of total binding. The binding reaction was terminated by rapid filtration onto 1% PEI pretreated GF/C filters using a Brandel Harvestor. Filters were placed in scintillation fluid and radioactivity assessed by liquid scintillation counting.

The present compounds were considered active at IC$_{50}$ values of 10 uM or lower. The present examples were all tested except for Examples 2, 3, 7, 8, 26 and 31. The compounds testing active had an IC$_{50}$ in a range of from about 3 nM to about 10 uM. Compounds 13, 14, 17, and 21 tested above 10 uM, the limit of the present assay.

EXAMPLES

Nuclear magnetic resonance spectra were recorded at either 300 or 400 MHz using, respectively, a Bruker ARX 300 or Bruker AVANCE 400 spectrometer. CDCl$_3$ is deuteriochloroform, DMSO-d$_6$ is hexadeuteriodimethylsulfoxide, and CD$_3$OD is tetradeuteriomethanol. Chemical shifts are reported in parts per million (Δ) downfield from the internal standard tetramethylsilane. Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz. Fourier transform infrared (FTIR) spectra were recorded on a Nicolet 510 infrared spectrometer. FTIR spectra were recorded in transmission mode, and band positions are reported in inverse wavenumbers (cm$^{-1}$). Mass spectra were taken on either a SCIEX5 or Micromass instruments, using electrospray (ES) ionization techniques. Elemental analyses were obtained using a Perkin-Elmer 240C elemental analyzer. Melting points were taken on a Thomas-Hoover melting point apparatus and are uncorrected. All temperatures are reported in degrees Celsius.

Analtech Silica Gel GF and E. Merck Silica Gel 60 F-254 thin layer plates were used for thin layer chromatography. Both flash and gravity chromatography were carried out on E. Merck Kieselgel 60 (230-400 mesh) silica gel. Analytical and preparative HPLC were carried out on Rainin or Beckman chromatographs. ODS refers to an octadecylsilyl derivatized silica gel chromatographic support. 5 u Apex-ODS indicates an octadecylsilyl derivatized silica gel chromatographic support having a nominal particle size of 5 u, made by Jones Chromatography, Littleton, Colo. YMC ODS-AQ® is an ODS chromatographic support and is a registered trademark of YMC Co. Ltd., Kyoto, Japan. PRP-1® is a polymeric (styrene-divinylbenzene) chromatographic support, and is a registered trademark of Hamilton Co., Reno, Nev.) Celite® is a filter aid composed of acid-washed diatomaceous silica, and is a registered trademark of Manville Corp., Denver, Colo.

The following examples are intended to be merely illustrative of the present invention and not limiting in any way.

Example 1

Preparation of Ethyl 3-(3-{(1S)-2-[(1,1-dimethyl-4-phenylbutyl)amino]-1-hydroxyethyl}-4,5-difluorophenyl)propanoate (a) Ethyl (2E)-3-(3,4-difluoro-5-hydroxyphenyl)-2-propenoate A 1 L round-bottomed flask was charged with a stir bar, 5-bromo-2,3-difluorophenol (48.3 g, 231 mmol) and propionitrile (460 mL). The solution was deoxygenated by bubbling nitrogen for 15 minutes. To this solution was added Pd(OAc)$_2$ (5.20 g, 23.2 mmol), P(O-tol)$_3$ (28.2 g, 92.5 mmol), ethyl acrylate (50 mL, 461 mmol) and diisopropylethylamine (161 mL, 924 mmol) sequentially. The flask was immersed into a preheated (120° C.) oil bath. The reaction was heated at this temperature for 22 h. Upon cooling to room temperature, the reaction mixture was filtered through a Celite-plugged filter frit, washed with CH$_2$Cl$_2$, and concentrated.

A second 1 L round-bottomed flask was charged with a stir bar, 5-bromo-2,3-difluorophenol (50.2 g, 240 mmol) and propionitrile (460 mL). The solution was deoxygenated by bubbling nitrogen for 15 minutes. To this solution was added Pd(OAc)$_2$ (5.42 g, 24.1 mmol), P(O-tol)$_3$ (29.3 g, 96.1 mmol), ethyl acrylate (52 mL, 480 mmol) and diisopropylethylamine (167 mL, 959 mmol) sequentially. The flask was immersed into a preheated (120° C.) oil bath. The reaction was heated at this temperature for 22 h. Upon cooling to room temperature, the reaction mixture was filtered through a Celite-plugged filter frit, washed with CH$_2$Cl$_2$, and concentrated.

The residues were combined and diluted with ethyl acetate and washed successively with two times 1N HCl and once with brine. The organic layer was dried over Na$_2$SO$_4$, filtered, and concentrated. The crude residue was purified by flash column chromatography eluting with 0-30% EtOAc in hexanes to afford the desired product (91.1 g) in 85% yield.

(b) Ethyl 3-(3,4-difluoro-5-hydroxyphenyl)propanoate

A 2 L Parr hydrogenation flask was charged with ethyl (2E)-3-(3,4-difluoro-5-hydroxyphenyl)-2-propenoate (91.1 g) and 750 mL of absolute ethanol. The solution was deoxygenated by bubbling nitrogen for 15 minutes. To this was added 10.15 g of catalyst (5% Pd/C—wet) and placed under hydrogen atmosphere (55 psi). After 21 h of stirring, starting material was still present so the reaction was filtered, washed with methanol and DCM and concentrated. The residue was diluted with 550 mL of absolute ethanol and deoxygenated by bubbling nitrogen for 30 minutes. An additional 9.32 g of 10% Pd/C (dry) was added and the reaction placed under hydrogen atmosphere (60 psi) for another 22 h. The reaction was still not complete. The reaction was then filtered as above and the residue was dissolved in 450 mL of ethanol and an additional 10 g of 10% Pd/C (dry) was added and the reaction placed under hydrogen atmosphere (60 psi) for another 20 h. The reaction was then filtered though a pad of Celite and washed with $CH_3OH$ and $CH_2Cl_2$ and concentrated to get the desired product (86.9 g) in 95% yield.

(c) Ethyl 3-(3,4-difluoro-5-{[(trifluoromethyl)sulfonyl]oxy}phenyl)propanoate

In a 2 L round bottom flask triethylamine (105 mL, 753 mmol) was added to a solution of compound ethyl 3-(3,4-difluoro-5-hydroxyphenyl)propanoate (86.9 g, 378 mmol) in $CH_2Cl_2$ (1000 mL) under $N_2$ and the reaction mixture cooled to 0° C. Trifluoromethanesulfonic anhydride (70 mL, 416 mmol) was added dropwise over 50 min. The reaction was allowed to warm slowly to room temperature overnight and stir for 3 days. The reaction mixture was washed three times with brine. The organic layer was dried over $Na_2SO_4$, filtered, and concentrated. Column chromatography (0-25% ethyl acetate:hexane and 0-100% $CH_2Cl_2$:hexane) afforded the desired product (93.8 g, 69%).

(d) Ethyl 3-(3-ethenyl-4,5-difluorophenyl)propanoate

To a solution of ethyl 3-(3,4-difluoro-5-{[(trifluoromethyl)sulfonyl]oxy}phenyl) propanoate (28.06 g, 77.5 mmol) in In a 1 L round bottom flask in DMF (380 mL, deoxygenated with $N_2$) under $N_2$ was added $(t-Bu_3P)_2Pd$ (5.95 g, 11.6 mmol), lithium chloride (9.85 g, 232 mmol), and vinyl(tributyl)tin (50 mL, 171 mmol). The reaction was stirred at RT for 22 h. Upon completion, ethyl acetate and KF (aq.) were added and the reaction stirred for an additional 2 h. The heterogeneous reaction mixture was filtered thru a Celite-plugged filter frit and rinsed with ethyl acetate. The layers were separated and the organic layer washed an additional time with KF. The combined aqueous layers were then back extracted with ethyl acetate. The combined organic layers were then washed with $H_2O$ and brine, dried over $Na_2SO_4$, filtered, and concentrated. Column chromatography (0-80% DCM:hexane) yielded the desired product (16.33 g, 88%).

(e) Ethyl 3-{3-[(1S)-1,2-dihydroxyethyl]-4,5-difluorophenyl}propanoate

A solution of AD-mix-α (66.0 g), t-BuOH (340 mL), and $H_2O$ (380 mL) was stirred until no solid was observed and then cooled to 0° C. Ethyl 3-(3-ethenyl-4,5-difluorophenyl) propanoate (16.3 g, 68.0 mmol) in t-BuOH (45 mL) and $H_2O$ (5 mL) was added and the reaction stirred at 0° C. for 6 h and then warmed to room temperature overnight. Sodium sulfite (84 g) was added and the reaction stirred at room temperature for 5 h. The reaction was diluted with $H_2O$ and extracted two times with $CH_2Cl_2$. The combined organic layers were dried over $Na_2SO_4$, filtered, and concentrated. Column chromatography (2-90% ethyl acetate:hexane) afforded the desired product (17.76 g, 95%).

(f) Ethyl 3-[3,4-difluoro-5-((1S)-1-hydroxy-2-{[(4-methylphenyl)sulfonyl]oxy}ethyl)phenyl]propanoate p-Toluenesulfonyl chloride (12.4 g, 64.8 mmol) in pyridine (35 mL) was added dropwise over 7 min to a cooled (−10 to −20° C.) solution of ethyl 3-{3-[(1S)-1,2-dihydroxyethyl]-4,5-difluorophenyl}propanoate (17.7 g, 64.8 mmol) in pyridine (70 mL) under $N_2$. The reaction was stirred at −10 to −20° C. for ~4.5 h. The reaction was quenched with ice $H_2O$ and stirred overnight. The reaction mixture was diluted with $H_2O$ and extracted three times with ethyl ether. The combined organic layers were washed with 1N HCl, aq. $CuSO_4$, and brine. The organic layer was dried over $MgSO_4$, filtered, and concentrated. Purification by column chromatography (0-80% ethyl acetate:hexane) afforded the desired product (22.5 g, 81%) along with some recovered starting material (2.13 g).

(g) Ethyl 3-{3,4-difluoro-5-[(2S)-2-oxiranyl] phenyl}propanoate

To a solution of ethyl 3-[3,4-difluoro-5-((1S)-1-hydroxy-2-{[(4-methylphenyl)sulfonyl]oxy}ethyl)phenyl]propanoate (22.5 g, 52.5 mmol) in absolute ethanol (430 mL) was added potassium carbonate (7.27 g, 52.6 mmol) and the reaction was stirred at RT for 4 days. The reaction was concentrated and diluted with water and extracted with ethyl acetate (×2). The combined organic layers were washed with water and brine. The organic layer was dried over $Na_2SO_4$, filtered, and concentrated. Purification by column chromatography (0-25% ethyl acetate:hexane) afforded the desired product (11.07 g, 82%).

(h) Ethyl 3-(3-{(1S)-2-[(1,1-dimethyl-4-phenylbutyl) amino]-1-hydroxyethyl}-4,5-difluorophenyl)propanoate A solution of ethyl 3-{3,4-difluoro-5-[(2S)-2-oxiranyl] phenyl}propanoate (11.07 g, 43.2 mmol) and (1,1-dimethyl-4-phenylbutyl)amine (7.68 g, 43.4 mmol) in ethanol (50 mL) was heated at 70° C. for 36 h. The reaction was concentrated and purified by column chromatography (0-90% ethyl acetate:hexane) afforded the desired product (14.54 g, 78%). MS (m/z): 434.2 (M+H).

Preparation of (1,1-Dimethyl-4-phenylbutyl)amine (a) Methyl-4-phenylbutyrate 1800 g (10.98 moles) of 4-phenylbutyric acid, crystalline in a glass bottle was heated with a heating blanket for 2 h to melt the acid. The liquid was poured in 8 L of methanol in a 22 L reaction flask (3-necked round-bottom flask fitted with stirrer and thermometer adapters). The solution was stirred under Argon, temperature 20° C.-33° C., and 400 mL concentrated sulfuric acid was added in 50 mL portions. The temperature increased to 49° C. The solution was stirred under argon over the week-end and allowed to cool to ambient temperature. The solution was transferred to a quench tank and diluted with 8 L of water. The oil formed was separated and the aqueous phase was extracted with 2×1 L of ethyl acetate. The extracts were combined with the oil and the solution concentrated to give 1753 g of clear oil in 90% yield.

(b) 1,1-Dimethyl-4-phenylbutanol

8 L of 3.0 M methylmagnesium chloride in ether was transferred to a 22 L 3-necked, round-bottomed flask using $N_2$ pressure. This flask was equipped with argon flow inlet. The solution had been chilled to 0° in an ice-acetone bath and 1283 g (7.2 moles) quantity of methyl-4-phenylbutyrate was added under argon over 4 h maintaining the temperature between 0° C. and 11° C. The reaction mixture was stirred for 1H and an aliquot was withdrawn, quenched in water and extracted with ether. The ether extract was concentrated and the residual oil was assayed by NMR spectrum. This confirmed that no starting material remained. The reaction mixture was rechilled to 0° and 4 L of water was added over 3 to 4H. This caused vigorous gas evolution and slurrying during the initial stages of the addition and caused precipitation of a white solid. The reaction mixture was stirred for 1H following the water addition and the mixture was then filtered using Buchner funnel and the filtrate was separated. The aqueous phase was extracted with 2 L of ether-hexane mixture and the organic phases combined and concentrated to give 1200 g of yellow oil 94% yield.

(c)
N-(1,1-dimethyl-4-phenylbutyl)-2-chloroacetamide 809 g chloroacetonitrile and 400 mL glacial acetic acid in a 5 L, 3-necked, round-bottomed flask equipped with stirrer, thermometer, "Y" adapter and one 500 mL pressure-equalizing addition funnel and cooled to –3° C. using an ice-acetone bath. A 600 g (3.37 moles) quantity of 1,1-dimethyl-4-phenylbutanol was added concurrently with 292.5 mL con. sulfuric acid over 1.5H while maintaining the temperature between –7° and +5° by adjusting the rates of the concurrent additions. The reaction mixture was stirred 15 min beyond the completion of additions and then quenched in ice-water with stirring in a quench tank. A heavy white precipitate formed which was dissolved in dichloromethane (4 L) with stirring. The organic phase was separated and the aqueous phase extracted with an additional 1 L of dichloromethane. The combined dichloromethane extracts were concentrated to give 842 g of white solid. A LC/MS analysis of the solid indicated an 80/10/10 composition, the major being the desired N-(1,1-dimethyl-4-phenylbutyl)-2-chloroacetamide and the two minor components being recovered alcohol and 1,1-dimethyltetralin, respectively. A crude yield of 98% was obtained.

(d) 1,1-Dimethyl-4-phenylbutylamine

A 1008 g quantity of N-(1,1-dimethyl-4-phenylbutyl)-2-chloroacetamide (3.98 moles) was dissolved in 8.4 L of ethanol and 1080 mL gl. acetic acid in a 22 L 3-necked, round-bottomed flask equipped with stirrer, thermometer and reflux condenser and 370 g (4.86 moles) of thiourea was added. The reaction was heated to reflux to dissolve the thiourea. A white crystalline precipitate began to form after about two hours of reflux. The reflux was continued for additional 8 h. The reaction mixture was allowed to cool to ambient temperature and was filtered and the filtrate diluted with 8 L of water, extracted with 2×1 L of hexane and neutralized by the addition of 220 mL 50% sodium hydroxide. This caused an oil to form which was separated and the aqueous phase extracted with 2×2 L of ether/hexane. The extracts were combined with the oil and concentrated to give 590 g of reddish oil, LC/MS single peak, m/e 179, NMR (CDCl$_3$) consistent with the desired product, 1,1-Dimethyl-4-phenylbutylamine, 84% crude yield. This material was vacuum distilled to give 518 g of clear oil, bp$_{(1\ torr)}$ 71-74°.

Example 2

Preparation of 3-(3-{(1S)-2-[(1,1-dimethyl-4-phenylbutyl)amino]-1-hydroxyethyl}-4,5-difluorophenyl) propanoic acid a) Zwitterion Sodium hydroxide (3N, 22.2 mL, 66.6 mmol) was added to a solution of ethyl 3-(3-{(1S)-2-[(1,1-dimethyl-4-phenylbutyl)amino]-1-hydroxyethyl}-4,5-difluorophenyl)propanoate (14.54 g, 33.6 mmol) in methanol (330 mL). The reaction was stirred at room temperature for 15 h. The methanol was removed in vacuo and the aqueous layer was diluted with water. The pH of the aqueous layer was adjusted to pH ~6.0 while stirring. The precipitated white solid was collected by filtration and dried under high vacuum in the oven (~55° C.) for ~20 h.

b) Hydrochloride Salt

The zwitterion is taken up in acetonitrile and 1N HCl in ether was added and stirred and then concentrated in vacuo to afford the desired product (14.31 g, 97%) as white foam solid. MS (m/z): 406.2 (M+H).). $^1$H NMR (400 MHz, DMSO-d$_6$) δ ppm 12.24 (br. s., 1 H) 9.01 (br. s., 1 H) 8.54 (br. s., 1 H) 7.12-7.36 (m, 7 H) 6.38 (d, J=3.79 Hz, 1 H) 5.20 (d, J=9.60 Hz, 1 H) 3.03 (br. s., 1 H) 2.95 (m, 1 H) 2.84 (t, J=7.71 Hz, 2 H) 2.45-2.70 (m, 4 H) 1.51-1.75 (m, 4 H) 1.28 (s, 6 H).

c) Trifluoroacetate Salt (1,1-dimethyl-4-phenylbutyl)amine (0.693 g, 3.91 mmol) in ethanol (1.8 mL) was added to a solution of ethyl 3-[3,4-difluoro-5-((1S)-1-hydroxy-2-{[(4-methylphenyl)sulfonyl]oxy}ethyl)phenyl]propanoate (1.53 g, 3.57 mmol) in ethanol (3.8 mL). The reaction vessel was sealed and heated at 90° C. for 22 h. The reaction was cooled to room temperature and sodium hydroxide (6N, 2.6 mL, 15.6 mmol) was added. The reaction was then stirred at room temperature for 24 h. The reaction mixture was concentrated to remove ethanol and purified using a Gilson Prep HPLC (5-95% CH$_3$CN/H$_2$O (w/0.1% TFA) to afford the desired product (0.570 g, 31% yield over 2 steps) as the TFA salt. MS (m/z): 406.0 (M+H).

d) Potassium Salt

Method A: Acetone (300 uL) was added to the crystalline parent 3-(3-{(1S)-2-[(1,1-dimethyl-4-phenylbutyl)amino]-1-hydroxyethyl}-4,5-difluorophenyl)propanoic acid (15.0 mg). To the solution, potassium hydroxide (3M in water, 1.1 equivalents, 13.6 uL) was added. The solution was heated to 50° C. and held for 4 hours with continuous stirring. The slurry was taken to 0° C. in 5° C. increments and held at each step for 30 minutes with continued stirring. Once at 0° C., the slurry was stirred overnight. The following morning the slurry was returned directly to room temperature. No solids were observed. The solution was cooled directly from room temperature to 0° C. Once at 0° C., the solution was pulse stirred (stirred for 30 seconds, then not stirred for 2 minutes) for ~3 days. The slurry was returned directly to room temperature and the solids were isolated, filtered and dried.

Method B: Acetone (10.0 mL) was added to the crystalline parent 3-(3-{(1S)-2-[(1,1-dimethyl-4-phenyl butyl)amino]-1-hydroxyethyl}-4,5-difluorophenyl)propanoic acid (414.95 mg), and the resulting slurry was stirred at RT for ~20 minutes. 1.05 equivalents of base (358.2 uL; 3M in water) were added to the slurry. The slurry began to clarify but the solid never completely dissolved. Upon adding an additional 5 mL of acetone, the potassium salt readily precipitated within a few minutes at RT. The product was filtered, washed with acetone (1 mL) and air-dried.

Example 3

Preparation of ethyl 3-[3-((1S)-2-{[2-(2,3-dihydro-1H-inden-2-yl)-1,1-dimethylethyl]amino}-1-hydroxyethyl)-4,5-difluorophenyl]propanoate (a) Ethyl 3-{3,4-difluoro-5-[(1S)-1-hydroxy-2-iodoethyl]phenyl}propanoate Sodium iodide (3.34 g, 22.3 mmol) was added to a solution of ethyl 3-[3,4-difluoro-5-((1S)-1-hydroxy-2-{[(4-methylphenyl)sulfonyl]oxy}ethyl)phenyl]propanoate (0.950 g, 2.22 mmol) in acetone (9.0 mL). The reaction mixture was heated at reflux for 18 h. The reaction was cooled to room temperature and concentrated. The residue was diluted with $H_2O$ and extracted two times with ethyl acetate. The combined organic layers were washed with $H_2O$ and brine, dried over $Na_2SO_4$, filtered, and concentrated. Column chromatography (0-40% ethyl acetate:hexane) afforded 0.552 g (65%) of product: $^1H$ NMR (400 MHz, chloroform-d) δ ppm 7.13 (d, J=5.81 Hz, 1 H) 7.01 (dd, J=10.61, 7.58 Hz, 1 H) 5.09 (dd, J=8.34, 3.54 Hz, 1 H) 4.15 (q, J=7.07 Hz, 2 H) 3.58 (dd, J=10.23, 3.16 Hz, 1 H) 3.41 (dd, J=10.36, 8.34 Hz, 1 H) 2.94 (t, J=7.58 Hz, 2 H) 2.62 (t, J=7.71 Hz, 2 H) 2.26 (s, 1 H) 1.26 (t, J=7.20 Hz, 3 H).

(b) Ethyl 3-[3-((1S)-2-{[2-(2,3-dihydro-1H-inden-2-yl)-1,1-dimethylethyl]amino}-1-hydroxyethyl)-4,5-difluorophenyl]propanoate To a solution of ethyl 3-{3,4-difluoro-5-[(1S)-1-hydroxy-2-iodoethyl]phenyl}propanoate (0.550 g, 1.43 mmol) in ethanol (2.8 mL) was added [2-(2,3-dihydro-1H-inden-2-yl)-1,1-dimethylethyl]amine (0.273 g, 1.44 mmol) and $K_2CO_3$ (0.218 g, 1.58 mmol). The reaction was heated at 90° C. for 17 h. Upon cooling, the reaction was filtered and concentrated. Column chromatography (0-12% $CH_3OH:CH_2Cl_2$) provided 0.315 g (49%) of the title compound: MS (ESI) 446.0 (M+H).

Example 4

Preparation of 3-[3-((1S)-2-{[2-(2,3-Dihydro-1H-inden-2-yl)-1,1-dimethylethyl]amino}-1-hydroxyethyl)-4,5-difluorophenyl]propanoic acid trifluoroacetate salt Sodium hydroxide (6N, 0.17 mL, 1.02 mmol) was added to a solution of ethyl 3-[3-((1S)-2-{[2-(2,3-dihydro-1H-inden-2-yl)-1,1-dimethylethyl]amino}-1-hydroxyethyl)-4,5-difluorophenyl]propanoate (0.312 g, 0.701 mmol) in ethanol (3.0 mL). The reaction was stirred at room temperature for 28 h. The reaction was concentrated in vacuo. Purification by reverse phase HPLC (5-95% $CH_3CN:H_2O$ with 0.1% TFA) yielded 0.191 g (51%) of the product as the TFA salt: $^1H$ NMR(400 MHz, DMSO-$d_6$) δ ppm 12.25(br. s., 1H) 8.59 (br. s., 1 H) 8.47 (br. s., 1H) 7.24-7.42 (m, 2 H) 6.99-7.24 (m, 4 H) 6.39 (d, J=3.79 Hz, 1 H) 5.15 (d, J=10.36 Hz, 1 H) 3.35 (br. s., 2 H) 3.08 (dd, J=14.65, 7.07 Hz, 3 H) 2.84 (t, J=7.58 Hz, 2 H) 2.58 (dd, J=14.91, 4.29 Hz, 2 H) 2.54-2.68 (m, 1 H) 1.95 (d, J=6.06 Hz, 1 H) 1.37 (s, 6 H); MS (ESI) 418.0 (M+H).

Example 5

Preparation of 5-(3-{(1S)-2-[(1,1-dimethyl-4-phenylbutyl)amino]-1-hydroxyethyl}-4,5-difluorophenyl)pentanoic acid hydrochloride salt (a) Ethyl 3-(3,4-difluoro-5-hydroxyphenyl)pentanoate A mixture of 5-bromo-2,3-difluorophenol (20 g 0.0957 mol), ethyl pentenoate (24.53 g, 0.191 mol), N,N-diisopropylamine (66.68 ml, 0.383 mol) and catalytic reagents [Pd (OAc)$_2$=2.15 g, 9.57 mmol; P(O-tol)$_3$=11.65 g, 0.0383 mol] in propionitrile (500 mL) in solution was degassed by bubbling nitrogen. The reactions were heated to 120° C. overnight. The reaction mixtures were filtered through a Celite and washed with $CH_2Cl_2$ and filtrates were combined and concentrated. The crude residue was purified by flash column chromatography eluting with 0-10% EtOAc in hexanes to afford the desired product (21.5 g). Subsequent hydrogenation in Parr shaker using Pd/C at 65 psi overnight, followed by filtration, concentration and column chromatography (0-10% ethyl acetate:hexane) afforded the desired product (17.6 g, 71%).

(b) Ethyl 3-(3,4-difluoro-5-{[(trifluoromethyl)sulfonyl]oxy}phenyl)pentanoate

To ethyl 5-(3,4-difluoro-5-hydroxyphenyl)pentanoate (9.35 g, 0.036 mol) material in DCM (180 mL) was added triethylamine (10.1 mL, 0.0724 mol) and the reaction mixture cooled to 0° C. Trifluoromethanesulfonic anhydride (6.70 mL, 0.0398 mol) was added dropwise. The reaction was allowed to warm slowly to room temperature overnight. The reaction mixture was washed three times with brine. The organic layer was dried, filtered, and concentrated. Column chromatography (9:1 hexane:ethyl acetate) afforded the desired product (12.54 g, 89%).

(c) Ethyl 3-(3-ethenyl-4,5-difluorophenyl)pentanoate

To a solution of ethyl 3-(3,4-difluoro-5-{[(trifluoromethyl)sulfonyl]oxy}phenyl) pentanoate (20.14 g, 51.6 mmol) in DMF (260 mL) under $N_2$ was added lithium chloride (6.56 g, 0.155 mol), (t-Bu$_3$P)$_2$Pd (3.96 g, 77.4 mmols), and vinyl(tributyl)tin (16.57 mL, 0.057 mol). The reaction was stirred at RT overnight. Upon completion, ethyl acetate and 10% KF (aq.) were added and the reaction stirred for an additional 2 h. The mixture was filtered thru a Celite-plugged filter frit and rinsed with ethyl acetate. The layers were separated and the organic layer washed an additional time with KF and filtered through celite to remove white fluffy solid. The aqueous layers were then back extracted with ethyl acetate. The combined organic layers were then washed with brine, dried, filtered, and concentrated. Column chromatography (hexane:ethyl acetate, 9:1) yielded the desired product (12.58 g, 91%).

(d) Ethyl 3-{3-[(1S)-1,2-dihydroxyethyl]-4,5-difluorophenyl}pentanoate

A solution of AD-mix-α (50.0 g), t-BuOH (250 mL), and $H_2O$ (280 mL) was stirred until no solid was observed and then cooled to 0° C. Ethyl 3-(3-ethenyl-4,5-difluorophenyl) pentanoate (12.58 g, 0.0469 mol) in t-BuOH (35 mL) and $H_2O$ (10 mL) was added and the reaction stirred at 0° C. for 6 h and then warmed to room temperature overnight. Sodium sulfite (64 g) was added to quench the reaction and the reaction was diluted with $H_2O$ and extracted three times with ethylacetate. The combined organic layers were dried over $Na_2SO_4$, filtered, and concentrated. Column chromatography (hexane:ethylacetate, 7:3) yielded the desired product (13.02 g, 92%).

(e) Ethyl 3-[3,4-difluoro-5-((1S)-1-hydroxy-2-{[(4-methylphenyl)sulfonyl]oxy}ethyl)phenyl]propanoate p-Toluenesulfonyl chloride (9.03 g, 0.0474 mol) in pyridine (25 mL) was added dropwise to a cooled (−15° C.) solution of ethyl 3-{3-[(1S)-1,2-dihydroxyethyl]-4,5-difluorophenyl}pentanoate (13.02 g, 0.043 mol) in pyridine (50 mL) under $N_2$. The reaction was stirred at −15° C. and warmed to RT overnight. The reaction mixture was quenched with $H_2O$ and extracted three times with ethyl ether. The combined ether layers were washed with 1N HCl, sat. $CuSO_4$, and brine. The organic layer was dried over Na$_2$SO$_4$, filtered, and concentrated. Column chromatography (hexane:ethylacetate, 0-30%) yielded the desired product (14.68 g, 75%).

(f) Ethyl 3-{3,4-difluoro-5-[(2S)-2-oxiranyl]phenyl}pentanoate

To a solution of ethyl 3-[3,4-difluoro-5-((1S)-1-hydroxy-2-{[(4-methylphenyl)sulfonyl]oxy}ethyl)phenyl]pentanoate (14.50 g, 0.0318 mol) in absolute ethanol (270 mL) was added potassium carbonate (8.78 g, 0.0635 mol) and the reaction was stirred at RT overnight. The reaction was concentrated and diluted with water and extracted with ethyl acetate (×2). The combined organic layers were dried over Na$_2$SO$_4$, filtered, and concentrated. Column chromatography (hexane:ethylacetate, 0-25%) yielded the desired product (8.65 g, 96%).

(g) Ethyl 3-(3-{(1S)-2-[(1,1-dimethyl-4-phenylbutyl)amino]-1-hydroxyethyl}-4,5-difluorophenyl)pentanoate Ethyl 3-{3,4-difluoro-5-[(2S)-2-oxiranyl]phenyl}pentanoate (8.56 g, 0.0301 mol) and (1,1-dimethyl-4-phenylbutyl)amine (5.39 g, 0.0304 mol) in ethanol (50 mL) was heated at 70° C. overnight. The reaction was concentrated and purified by column chromatography (0-40% ethyl acetate:hexane) yield the desired product (9.53 g, 69%). MS (m/z): 434.2 (M+H).

(h) 5-(3-{(1S)-2-[(1,1-Dimethyl-4-phenylbutyl)amino]-1-hydroxyethyl}-4,5-difluorophenyl)pentanoic acid hydrochloride salt Sodium hydroxide (3N, 20 mL, 0.0611 mol) was added to a solution of ethyl 3-(3-{(1S)-2-[(1,1-dimethyl-4-phenylbutyl)amino]-1-hydroxyethyl}-4,5-difluorophenyl)pentanoate (9.4 g, 0.0204 mol) in ethanol (150 mL). The reaction was stirred at room temperature overnight. The ethanol was removed in vacuo and the aqueous layer was diluted with water. The pH of the aqueous layer was adjusted to pH ~6.0 with 6N HCl while stirring. The precipitated white solid was collected by decanting the aqueous solution and dissolving in DCM, dried over Na$_2$SO$_4$, filtered and concentrated. The zwitterion was taken up in acetonitrile and 1N HCl in ether was added, stirred and then concentrated in vacuo to afford the desired product (8.63 g) as a gummy solid. MS (m/z): 434.2 (M+H).

Example 6

Preparation of 5-[3-((1S)-2-{[2-(2,3-dihydro-1H-inden-2-yl)-1,1-dimethylethyl]amino}-1-hydroxyethyl)-4,5-difluorophenyl]pentanoic acid hydrochloride salt The title compound was prepared by substituting [2-(2,3-dihydro-1H-inden-2-yl)-1,1-dimethylethyl]amine for (1,1-dimethyl-4-phenylbutyl)amine in step (g) of Example 5: MS (m/z): 446.2 (M+H).

Example 7

Preparation of 4-(3-{(1S)-2-[(1,1-dimethyl-4-phenylbutyl)amino]-1-hydroxyethyl}-4,5-difluorophenyl)butanoic acid trifluoroacetate salt The title compound was prepared by substituting methyl 3-butenoate for ethyl acrylate in step (a) of Example 1. Purification by reverse phase HPLC yielded the desired product: MS (m/z): 420.2 (M+H).

Example 8

Preparation of 4-[3-((1S)-2-{[2-(2,3-dihydro-1H-inden-2-yl)-1,1-dimethylethyl]amino}-1-hydroxyethyl)-4,5-difluorophenyl]butanoic acid trifluoroacetate salt The title compound was prepared by substituting ethyl 4-pentenoate for ethyl acrylate in step a and [2-(2,3-dihydro-1H-inden-2-yl)-1,1-dimethylethyl]amine for (1,1-dimethyl-4-phenylbutyl)amine in step (h) of Example 1. Purification by reverse phase HPLC yielded the desired product: MS (m/z): 432.2 (M+H).

Example 9

Preparation of 3-{3-[(S)-2-({1,1-dimethyl-2-[4-(methyloxy)phenyl]ethyl}amino)-1-hydroxyethyl]-4,5-difluorophenyl}propanoic acid hydrochloride salt The title compound was prepared by substituting {1,1-dimethyl-2-[4-(methyloxy)phenyl]ethyl}amine for (1,1-dimethyl-4-phenylbutyl)amine in step (h) of Example 1: MS (m/z): 408 (M+H).

Preparation of {1,1-dimethyl-2-[4-(methyloxy)phenyl]ethyl}amine (a) Ethyl 2,2-dimethyl-3-(4-methoxyphenyl)propanoate Ethyl iso-butyrate (35.0 g, 0.30 mol) was added to a solution of lithium N,N-diisopropyl amide (prepared from N,N-diisopropylamine (38.1 g, 0.38 mol) and n-BuLi (207 mL, 0.33 mol, 1.6 M solution in hexanes)) in dry tetrahydrofuran (1 L) at −78° C. over a 30 min period under N$_2$ atmosphere. After the addition was complete, the reaction was stirred for 1 h after which HMPA (100 mL), NaI (67.0 g, 0.44 mol) and 4-methoxybenzyl chloride (39.3 g, 0.25 mol) were added sequentially. The reaction was then warmed to room temperature and stirred for additional 16 h before quenching at 0° C. with saturated NH$_4$Cl solution (250 mL) and the mixture was extracted with EtOAc (2×1 L). The combined organic layers were washed successively with 2 N HCl (2×300 mL), saturated sodium bicarbonate solution (2×300 mL), and brine (400 mL), dried over Na$_2$SO$_4$ and filtered. Concentration of the filtrate and purification of the resulting residue by flash column chromatography (silica gel, 100:0 to 96:4 hexane/EtOAc) afforded 54.0 g (90%) of ethyl 2,2-dimethyl-3-(4-methoxyphenyl)propanoate as a light yellow oil; $^1$H NMR (200 MHz, CDCl$_3$) δ 7.03 (d, J=8.7 Hz, 2H), 6.79 (d, J=8.7 Hz, 2H), 4.10 (q, J=7.3 Hz, 2H), 3.78 (s, 3H), 2.78 (s, 2H), 1.23 (t, J=7.3 Hz, 3H), 1.15 (s, 6H).

(b) 2,2-Dimethyl-3-(4-methoxyphenyl)propanoic acid

Potassium tert-butoxide (38.0 g, 0.34 mol) was added to a solution of ethyl 2,2-dimethyl-3-(4-methoxyphenyl)propanoate (40.0 g, 0.17 mol) in a mixture of water (4 mL) and tetrahydrofuran (800 mL) at room temperature and stirred for 16 h. The pH of the reaction mixture was adjusted to ~2 with 2 N HCl (250 mL) and extracted with EtOAc (800 mL). Aqueous layer was saturated with NaCl and extracted again with EtOAc (800 mL). The combined organic layers were washed with brine (350 mL), dried over $Na_2SO_4$, and concentrated to afford 34.0 g (96%) of 2,2-dimethyl-3-(4-methoxyphenyl)propanoic acid as a gummy oil; $^1$H NMR (200 MHz, $CDCl_3$) δ 7.08 (d, J=8.4 Hz, 2H), 6.80 (d, J=8.4 Hz, 2H), 3.78 (s, 3H), 2.83 (s, 2H), 1.19 (s, 6H).

(c) 2-Methyl-1-(4-methoxyphenyl)-2-propanamine

To a solution of 2,2-dimethyl-3-(4-methoxyphenyl)propanoic acid (36.0 g, 0.17 mol) in toluene (160 mL) was added triethylamine (19.2 g, 0.19 mol) and cooled to 0° C. To this cooled mixture was added diphenylphosphoryl azide (52.3 g, 0.19 mol) and the reaction mixture was stirred at room temperature for 15 min and then heated at 75° C. for 2.5 h. The progress of the reaction was monitored by TLC. After the completion of the reaction, as indicated by TLC it was cooled to room temperature and quenched with water (500 mL) and extracted with EtOAc (2×500 mL). The organic extracts were combined and dried over $Na_2SO_4$, filtered and concentrated to give an oil. This oil was dissolved in a mixture of 1,4-dioxane (108 mL) and 6 N HCl (180 mL) and heated at reflux for 1 h. After 1 h, the reaction mixture was cooled to room temperature and diluted with water (100 mL) and dichloromethane (400 mL). The organic layer was separated and pH of the aqueous layer was adjusted to ~14 with 6 M NaOH (200 mL) and extracted with dichloromethane (3×500 mL). The combined organic extracts were dried over $Na_2SO_4$, filtered and concentrated to give 20.0 g (65%) of 2-methyl-1-(4-methoxyphenyl)-2-propanamine as a yellow oil; $^1$H NMR (200 MHz, $CDCl_3$) δ 7.10 (d, J=8.4 Hz, 2H), 6.84 (d, J=8.4 Hz, 2H), 3.79 (s, 3H), 2.59 (s, 2H), 1.10 (s, 6H).

(d) 2-Methyl-1-(4-methoxyphenyl)-2-propanamine hydrochloride

2-Methyl-1-(4-methoxyphenyl)-2-propanamine (19.0 g, 0.10 mol) was dissolved in tert-butyl methyl ether (200 mL) and cooled to 0° C. A solution of 1.3 M HCl in 1,4-dioxane (85 mL) was added through an addition funnel over a period of 10 min. After the addition was complete, stirring was continued for additional 20 min at 0° C. The resulting precipitate was collected by filtration through a sintered glass funnel. The solid was washed with tert-butyl methyl ether (3×50 mL), and dried in vacuum oven for 30 h at 40° C. to afford 21.0 g (92%) of 2-methyl-1-(4-methoxyphenyl)-2-propanamine hydrochloride as a white solid; $^1$H NMR (200 MHz, DMSO-$d_6$) δ 7.14 (d, J=8.4 Hz, 2H), 6.88 (d, J=8.4 Hz, 2H), 3.72 (s, 3H), 2.80 (s, 2H), 1.17 (s, 6H); $^{13}$C NMR (50 MHz, DMSO-$d_6$) δ 158.1, 131.4, 127.2, 113.6, 54.9, 53.7, 44.1, 24.6; ESI MS m/z 180 $[C_{11}H_{17}NO+H]^+$.

Example 10

Preparation of 3-(3-{(1S)-2-[(1,1-dimethyl-5-phenyl pentyl)amino]-1-hydroxyethyl}-4,5-difluorophenyl) propanoic acid hydrochloride salt The title compound was prepared by substituting (1,1-dimethyl-5-phenylpentyl)amine for (1,1-dimethyl-4-phenylbutyl)amine in step (h) of Example 1: MS (m/z): 420 (M+H). The amine (1,1-dimethyl-5-phenylpentyl)amine was prepared following the Scheme 2 and using procedures detailed in Example 9.

Example 11

Preparation of 3-[3-((1S)-2-{[2-(4-chloro-3-fluorophenyl)-1,1-dimethylethyl]amino}-1-hydroxyethyl)-4,5-difluorophenyl]propanoic acid hydrochloride salt The title compound was prepared by substituting [2-(4-chloro-3-fluorophenyl)-1,1-dimethylethyl]amine for (1,1-dimethyl-4-phenylbutyl)amine in step (h) of Example 1: MS (m/z): 430 (M+H). The amine [2-(4-chloro-3-fluorophenyl)-1,1-dimethylethyl]amine was prepared following the Scheme 2 and using procedures detailed in Example 9.

Example 12

Preparation of 3-[3-((1S)-2-{[1,1-dimethyl-2-(2-naphthalenyl)ethyl]amino}-1-hydroxyethyl)-4,5-difluorophenyl]propanoic acid hydrochloride salt The title compound was prepared by substituting [1,1-dimethyl-2-(2-naphthalenyl)ethyl]amine for (1,1-dimethyl-4-phenylbutyl)amine in step h of example 1: MS (m/z): 428 (M+H). The amine [1,1-dimethyl-2-(2-naphthalenyl)ethyl]amine was prepared following the Scheme 2 and using procedures detailed in Example 9.

Example 13

Preparation of 3-(3-{(1S)-2-[(1,1-dimethyl-2-phenylethyl)amino]-1-hydroxyethyl}-4,5-difluorophenyl) propanoic acid hydrochloride salt The title compound was prepared by substituting (1,1-dimethyl-2-phenylethyl)amine for (1,1-dimethyl-4-phenylbutyl)amine in step (h) of Example 1: MS (m/z): 378 (M+H). The amine (1,1-dimethyl-2-phenylethyl)amine was prepared using procedures following scheme 2 detailed in Example 9.

Example 14

Preparation of 3-(3,4-difluoro-5-{(1S)-1-hydroxy-2-[(1-methyl-1-phenylethyl)amino]ethyl}phenyl)propanoic acid hydrochloride salt The title compound was prepared by substituting (1-methyl-1-phenylethyl)amine for (1,1-dimethyl-4-phenylbutyl)amine in step (h) of Example 1: MS (m/z): 420 (M+H). The amine (1-methyl-1-phenylethyl)amine was prepared following Scheme 2 and using procedures detailed in Example 9.

Example 15

Preparation of 3-[3-((1S)-2-{[2-(4-chloro-2-fluorophenyl)-1,1-dimethylethyl]amino}-1-hydroxyethyl)-4,5-difluorophenyl]propanoic acid hydrochloride salt The title compound was prepared by substituting [2-(4-chloro-2-fluorophenyl)-1,1-dimethylethyl]amine for (1,1-dimethyl-4-phenylbutyl)amine in step (h) of Example 1: MS (m/z): 430 (M+H). The amine [2-(4-chloro-2-fluorophenyl)-1,1-dimethylethyl]amine was prepared following Scheme 2 and using procedures detailed in Example 9.

Example 16

Preparation of 3-[3-((1S)-2-{[1,1-dimethyl-2-(5-methyl-2-thienyl)ethyl]amino}-1-hydroxyethyl)-4,5-difluorophenyl]propanoic acid hydrochloride salt The title compound was prepared by substituting [1,1-dimethyl-2-(5-methyl-2-thienyl)ethyl]amine for (1,1-dimethyl-4-phenylbutyl)amine in step (h) of Example 1: MS (m/z): 398 (M+H). The amine [1,1-dimethyl-2-(5-methyl-2-thienyl)ethyl]amine was prepared following Scheme 2 and using procedures detailed in Example 9.

Example 17

Preparation of 3-{3-[(1S)-2-([1,1-dimethyl-3-[4-(methyloxy)phenyl]propyl}amino)-1-hydroxyethyl]-4,5-difluorophenyl]propanoic acid hydrochloride salt The title compound was prepared by substituting {1,1-dimethyl-3-[4-(methyloxy)phenyl]propyl}amine for (1,1-dimethyl-4-phenylbutyl)amine in step (h) of Example 1: MS (m/z): 422 (M+H). The amine {1,1-dimethyl-3-[4-(methyloxy)phenyl]propyl}amine was prepared following Scheme 2 and using procedures detailed in Example 9.

Example 18

Preparation of 3-[3,4-difluoro-5-((1S)-2-{[2-(3-fluoro-4-methylphenyl)-1,1-dimethylethyl]amino}-1-hydroxyethyl)phenyl]propanoic acid hydrochloride salt The title compound was prepared by substituting [2-(3-fluoro-4-methylphenyl)-1,1-dimethylethyl]amine for (1,1-dimethyl-4-phenylbutyl)amine in step (h) of Example 1: MS (m/z): 410 (M+H). The amine [2-(3-fluoro-4-methylphenyl)-1,1-dimethylethyl]amine was prepared following Scheme 2 and using procedures detailed in Example 9.

Example 19

Preparation of 3-{3-[(1S)-2-({1,1-dimethyl-2-[4-(methylthio)phenyl]ethyl}amino)-1-hydroxyethyl]-4,5-difluorophenyl}propanoic acid hydrochloride salt The title compound was prepared by substituting {1,1-dimethyl-2-[4-(methylthio)phenyl]ethyl}amine for (1,1-dimethyl-4-phenylbutyl)amine in step (h) of Example 1: MS (m/z): 424 (M+H). The amine {1,1-dimethyl-2-[4-(methylthio)phenyl]ethyl}amine was prepared following Scheme 2 and using procedures detailed in Example 9.

Example 20

Preparation of 3-{3-[(1S)-2-({2-[4-(1,1-dimethylethyl)phenyl]-1,1-dimethylethyl}amino)-1-hydroxyethyl]-4,5-difluorophenyl}propanoic acid hydrochloride salt The title compound was prepared by substituting {2-[4-(1,1-dimethylethyl)phenyl]-1,1-dimethylethyl}amine for (1,1-dimethyl-4-phenylbutyl)amine in step (h) of Example 1: MS (m/z): 434 (M+H). The {2-[4-(1,1-dimethylethyl)phenyl]-1,1-dimethylethyl}amine was prepared following Scheme 2 and using procedures detailed in Example 9.

Example 21

Preparation of 3-[3-((1S)-2-{[1,1-dimethyl-2-(2-thienyl)ethyl]amino}-1-hydroxyethyl)-4,5-difluorophenyl]propanoic acid hydrochloride salt The title compound was prepared by substituting [1,1-dimethyl-2-(2-thienyl)ethyl]amine for (1,1-dimethyl-4-phenylbutyl)amine in step (h) of Example 1: MS (m/z): 384 (M+H). The [1,1-dimethyl-2-(2-thienyl)ethyl]amine was prepared following Scheme 2 and using procedures detailed in Example 9.

Example 22

Preparation of 3-(3-{(1S)-2-[(1,1-dimethyl-3-phenylpropyl)amino]-1-hydroxyethyl}-4,5-difluorophenyl)propanoic acid hydrochloride salt The title compound was prepared by substituting (1,1-dimethyl-3-phenylpropyl)amine for (1,1-dimethyl-4-phenylbutyl)amine in step (h) of Example 1: MS (m/z): 392 (M+H). The (1,1-dimethyl-3-phenylpropyl)amine was prepared following Scheme 2 and using procedures detailed in Example 9.

Example 23

Preparation of 3-[3-((1S)-2-{[2-(4-bromophenyl)-1,1-dimethylethyl]amino}-1-hydroxyethyl)-4,5-difluorophenyl]propanoic acid hydrochloride salt The title compound was prepared by substituting [2-(4-bromophenyl)-1,1-dimethylethyl]amine for (1,1-dimethyl-4-phenylbutyl)amine in step (h) of Example 1: MS (m/z): 456 (M+H). The [2-(4-bromophenyl)-1,1-dimethylethyl]amine was prepared following Scheme 2 and using procedures detailed in Example 9.

Example 24

Preparation of 3-[3-((1S)-2-{[2-(5-chloro-2-thienyl)-1,1-dimethylethyl]amino}-1-hydroxyethyl)-4,5-difluorophenyl]propanoic acid hydrochloride salt The title compound was prepared by substituting [2-(5-chloro-2-thienyl)-1,1-dimethylethyl]amine for (1,1-dimethyl-4-phenylbutyl)amine in step (h) of Example 1: MS (m/z): 418 (M+H). The [2-(5-chloro-2-thienyl)-1,1-dimethylethyl]amine was prepared following Scheme 2 and using procedures detailed in Example 9.

Example 25

Preparation of 2-(3-{(1S)-2-[(1,1-dimethyl-4-phenylbutyl)amino]-1-hydroxyethyl}-4,5-difluorophenyl)-2-methylpropanoic acid hydrochloride salt (a)
5-Bromo-1,2-difluoro-3-[(phenylmethyl)oxy]benzene A solution of DMF (100 mL), 5-bromo-2,3-difluorophenol (10 g, 47.85 mol), and $K_2CO_3$ (7.27 g, 52.63 mol) and benzyl bromide (9 g, 52.63 mol) were combined at 0° C. under $N_2$.

The solution was allowed to warm to rt and stirred overnight. H₂O, Et₃N (2 eq) and EtOAc (5000 mL) were added and the organic layer separated. The aqueous layer was washed with EtOAc (2×) and the combined organic fractions were washed with 1M HCl (2×), sat. aq. NaHCO₃ (2×), dried, and concentrated. The crude product was purified by Biotage (gradient 100% hexanes-60% EtOAc/hexanes) to afford 10.08 g of product as an oil.

(b) Ethyl {3,4-difluoro-5-[(phenylmethyl)oxy]phenyl}acetate 5-bromo-1,2-difluoro-3-[(phenylmethyl)oxy]benzene (10 g, 33.3 mmol), diethyl propanedioate (6.9 g, 43.3 mmol), Cs₂CO₃ (108 g, 333 mmol), and dioxane (200 mL) were combined in a sealed flask and N₂ was bubbled through the solution for 15 minutes. Pd(t-Bu₃P)₂ (1.7 g, 3.33 mmol) was then added and the flask was sealed. The solution was heated to 80° C. and stirred vigorously. After 8 h, the temperature was increased to 120° C. After 3 days, it was cooled and H₂O and EtOAc were added. The aqueous layer washed with EtOAc (3×). The combined organic extracts were concentrated, and purified by Biotage (in two batches) to afford 1.82 g of the title compound (21%).

(c) Ethyl 2-{3,4-difluoro-5-[(phenylmethyl)oxy]phenyl}-2-methyl propanoate

A THF (4 mL) solution of ethyl {3,4-difluoro-5-[(phenylmethyl)oxy]phenyl}acetate (200 mg, 0.653 mmol) was cooled to −78° C. Potassium bis(trimethylsilyl)amide (KHMDS), 0.5M in toluene, 3.6 mL, 1.8 mmol, was added. The resultant solution was stirred for 60 min at −78° C. MeI (0.12 mL, 1.959 mmol) was added and the solution was warmed to rt overnight. To the reaction mixture was added sat. aq. NH₄Cl was added and the product extracted with EtOAc (3×), dried (Na₂SO₄), concentrated and purified by Biotage purification system (gradient 100% hexanes-20% EtOAc/hexanes) to afford 110 mg of product as an oil (52%).

(d) Ethyl 2-(3,4-difluoro-5-hydroxyphenyl)-2-methylpropanoate

A solution of ethyl 2-{3,4-difluoro-5-[(phenylmethyl)oxy]phenyl}-2-methylpropanoate (111 mg, 0.332 mmoles) in EtOH (2 mL) was degassed and flushed with N₂. To the solution was added Pd/C (10% by weight) and a H₂ balloon was attached. After overnight under H₂, the solution was filtered through celite and concentrated to afford 95 mg of crude product purified by Biotage.

(e) Ethyl 2-{3,4-difluoro-5-[(trifluoroacetyl)oxy]phenyl}-2-methylpropanoate

Triethylamine (0.1 mL, 0.66 mmol), ethyl 2-(3,4-difluoro-5-hydroxyphenyl)-2-methylpropanoate from step d in CH₂Cl₂ (3 mL) was cooled to 0° C. Trifluoromethanesulfonic anhydride (0.06 mL, 0.362 mmol) was added dropwise over 5 min. The reaction was allowed to warm slowly to room temperature overnight. The reaction mixture was diluted with DCM, washed three times with brine. The organic layer was dried over Na₂SO₄. Biotage purification (0-20% ethyl acetate:hexane) afforded the desired product (113 mg, 99%).

(f) Ethyl 2-(3-ethenyl-4,5-difluorophenyl)-2-methylpropanoate

To a solution of ethyl 2-{3,4-difluoro-5-[(trifluoroacetyl)oxy]phenyl}-2-methylpropanoate (113 mg, 0.332 mmol) in DMF (6 mL, deoxygenated with N₂) under N₂ was added (t-Bu₃P)₂Pd (25 mg, 0.05 mmol), lithium chloride (42 mg, 0.996 mmol), and vinyl(tributyl)tin (0.11 mL, 0.365 mmol). The reaction was stirred at room temperature for 22 hours. To the reaction mixture was added ethyl acetate and 20% KF (aq.) and the reaction stirred for an additional 2 h. The suspension was filtered through and rinsed with ethyl acetate. The organic layer was washed with 20% KF (aq.). The combined aqueous layers were washed with ethyl acetate. The combined organic layers were then washed with H₂O and brine, dried, and purified by Biotage purification system using (0-80% DCM:hexane) yielded the desired product (50 mg, 60%).

(g) 2-(3-{(1S)-2-[(1,1-Dimethyl-4-phenylbutyl)amino]-1-hydroxyethyl}-4,5-difluorophenyl)-2-methylpropanoic acid The title compound was prepared by substituting ethyl 2-(3-ethenyl-4,5-difluorophenyl)-2-methylpropanoate for ethyl 3-(3-ethenyl-4,5-difluorophenyl)propanoate in step (e) of Example 1. LCMS (m/z)=456.5 [M+H].

Example 26

Preparation of 2-[3-((1S)-2-{[2-(2,3-dihydro-1H-inden-2-yl)-1,1-dimethylethyl]amino}-1-hydroxyethyl)-4,5-difluorophenyl]-2-methylpropanoic acid hydrochloride salt The title compound was prepared by following the general procedure of Example 1 except substituting ethyl 2-(3-ethenyl-4,5-difluorophenyl)-2-methylpropanoate for ethyl 3-(3-ethenyl-4,5-difluorophenyl)propanoate in step (e) and [2-(2,3-dihydro-1H-inden-2-yl)-1,1-dimethylethyl]amine for (1,1-dimethyl-4-phenylbutyl)amine in step (h). MS (m/z): 468.5 (M+H).

Example 27

Preparation of 3-(4-Chloro-3-{(1S)-2-[(1,1-dimethyl-4-phenylbutyl)amino]-1-hydroxyethyl}phenyl)propanoic acid trifluoroacetate salt (a) (2-Chloro-5-iodophenyl)methanol A solution of 2-chloro-5-iodobenzoic acid (28 g, 99 mmoles) and toluene (198 mL) was cooled to 0° C. A 1M diisobutyl aluminium hydride (DIBAL) solution in toluene 208 mL, 208 mmol) solution was added drop wise over 20 minutes. The solution was allowed to slowly warm to rt. After 16 h the solution was cooled to 0° C., MeOH and 1M HCl was slowly added (exothermic reaction). The solution became clumpy and was filtered and the clumps washed with EtOAc. The organic phase was then isolated and the aqueous layer washed with EtOAc. The combined organic extracts were then washed with brine, dried (Na₂SO₄), and concentrated. The product was purified by Biotage chromatography (0%-100% EtOAc/Hexanes) to afford 9.01 g of product as a solid (34%). ¹H NMR (400 MHz, chloroform-d) δ ppm 7.85 (d, J=2.02 Hz, 1 H) 7.55 (dd, J=8.34, 2.27 Hz, 1 H) 7.09 (d, J=8.34 Hz, 1 H) 4.74 (s, 2 H) 2.25 (s, 1 H).

(b) 2-Chloro-5-iodobenzaldehyde

A methylene chloride solution (99 mL) of (2-chloro-5-iodophenyl)methanol (9.01 g, 33.5 mmol) and PCC (8.67 g, 40.2 mmol) were combined and stirred at rt. After 16 h, Et$_2$O was added and the solution stirred for 30 minutes. The solution was then filtered and the organic layer was washed with H$_2$O (2×), NaHCO$_3$ (3×), and brine. The organic layer was dried (Na$_2$SO$_4$), concentrated, and purified by Biotage chromatography (0%-20% EtOAc/hexanes) to afford 5.94 g of product (67%). $^1$H NMR (400 MHz, chloroform-d) δ ppm 10.38 (s, 1 H) 8.22 (d, J=2.02 Hz, 1 H) 7.83 (dd, J=8.46, 2.15 Hz, 1 H) 7.21 (d, J=8.59 Hz, 1 H).

(c) 1-Chloro-4-iodo-2-vinylbenzene

Ph$_3$PMeBr (9.10 g, 25.47 mmol) was added to anhydrous THF (34 mL) under N$_2$ and then cooled to −78° C. KHMDS (1 M solution, 25.47 mL, 25.47 mmol) was slowly added to the solution and the resultant solution was stirred at −78° C. for 1 h. 2-chloro-5-iodobenzaldehyde (4.86 g, 22.14 mmol) in THF (10 mL) was then slowly added and the resultant solution allowed to warm slowly to room temperature overnight. After 16 h, saturated aqueous NH$_4$Cl was added and the crude product extracted with EtOAc (3×). The combined organic extracts were dried (Na$_2$SO$_4$), concentrated, and purified by Biotage chromatography (0%-20% EtOAc/hexanes) to afford 4.32 g of product as an oil that solidifies (90%). $^1$H NMR (400 MHz, chloroform-d) δ ppm 7.87 (d, J=2.27 Hz, 1 H) 7.50 (dd, J=8.34, 2.27 Hz, 1 H) 7.09 (d, J=8.34 Hz, 1 H) 6.99 (dd, J=17.56, 10.99 Hz, 1 H) 5.74 (d, J=17.43 Hz, 1 H) 5.43 (d, J=11.12 Hz, 1 H).

(d) (1S)-1-(2-Chloro-5-iodophenyl)ethane-1,2-diol

1-Chloro-4-iodo-2-vinylbenzene (2.43 g, 9.19 mmol) was dissolved in t-BuOH/H$_2$O (1:1, 60 mL) and then cooled to 0° C. AD-mix-α (11 g) was slowly added. The reaction slowly warmed to rt overnight. Sodium sulfite (11 g) was added and the solution stirred at rt. After 3 h, H$_2$O and CH$_2$Cl$_2$ were added and the organic layer isolated. The aqueous layer was washed with CH$_2$Cl$_2$ (3×) and then the combined organic extracts were combined, dried (Na$_2$SO$_4$), concentrated, and purified by Biotage chromatography (0%-100% EtOAc/hexanes) to afford 2.6 g of (1S)-1-(2-chloro-5-iodophenyl)ethane-1,2-diol as an oil that will solidify over time (95%). $^1$H NMR (400 MHz, chloroform-d) δ ppm 7.94 (d, J=2.27 Hz, 1 H) 7.55 (dd, J=8.34, 2.02 Hz, 1 H) 7.07 (d, J=8.34 Hz, 1 H) 5.17 (dd, J=7.58, 3.03 Hz, 1 H) 3.90 (dd, J=11.24, 3.16 Hz, 1 H) 3.54 (dd, J=11.24, 7.71 Hz, 1 H) 3.49 (s, 2 H).

(e) Ethyl (2E)-3-{4-chloro-3-[(1S)-1,2-dihydroxyethyl]phenyl}acrylate (1S)-1-(2-chloro-5-iodophenyl)ethane-1,2-diol (2.60 g, 8.71 mmol), propionitrile (87 mL), ethyl acrylate (1.24 mL, 11.32 mmol), and triethylamine (3.6 mL, 26.13 mmol) were combined and N$_2$ was flushed through the solution for 10 minutes. Then Pd(OAc)$_2$ (587 mg, 0.871 mmol) and P(O-tol)$_3$ (1.06 g, 3.48 mmol) were added and the solution was heated to 80° C. After 16 h, the solution was cooled to rt and then EtOAc was added. The solution was washed with 1N HCl (2×), brine, dried, concentrated, and purified by Biotage chromatography (0%-100% EtOAc/hexanes) to afford 1.90 g of product as an oil (81%). $^1$H NMR (400 MHz, chloroform-d) δ ppm 7.79 (d, J=1.77 Hz, 1 H) 7.65 (d, J=16.17 Hz, 1 H) 7.34-7.40 (m, 2 H) 6.45 (d, J=15.92 Hz, 1 H) 5.24 (ddd, J=7.39, 2.84, 2.65 Hz, 1 H) 4.27 (q, J=7.24 Hz, 2 H) 3.89-3.97 (m, 1 H) 3.57 (ddd, J=11.49, 7.45, 4.55 Hz, 1 H) 2.87 (d, J=3.28 Hz, 1 H) 2.18 (d, J=5.81 Hz, 1 H) 2.05 (s, 3 H) 1.34 (t, J=7.20 Hz, 2 H).

(f) Ethyl 3-{4-chloro-3-[(1S)-1,2-dihydroxyethyl]phenyl}propanoate

Ethyl (2E)-3-{4-chloro-3-[(1S)-1,2-dihydroxyethyl]phenyl}acrylate (1.90 g, 7.02 mmol) was dissolved in EtOH and then degassed (3×) with N$_2$. Rh/Al$_2$CO$_3$ was added and then the solution was degassed again and then a H$_2$ balloon was attached. After 16 h of stirring at rt, the solution was filtered through celite, concentrated, and purified by Biotage chromatography (0%-25% EtOAc/hexanes) to afford 1.41 g of product as an oil (74%). $^1$H NMR (400 MHz, chloroform-d) δ ppm 7.45 (d, J=2.02 Hz, 1 H) 7.25 (d, J=8.08 Hz, 1 H) 7.08 (dd, J=8.08, 2.27 Hz, 1 H) 5.21 (dd, J=7.83, 3.03 Hz, 1 H) 4.13 (q, J=7.16 Hz, 2 H) 3.90 (dd, J=11.37, 3.28 Hz, 1 H) 3.56 (dd, J=11.37, 7.83 Hz, 1 H) 2.94 (t, J=7.71 Hz, 2 H) 2.62 (t, J=7.83 Hz, 2 H) 1.24 (t, J=7.20 Hz, 3 H).

(g) Ethyl 3-[4-chloro-3-((1S)-1-hydroxy-2-{[(4-methylphenyl)sulfonyl]oxy}ethyl)phenyl]propanoate p-Toluenesulfonyl chloride (1.08 g, 5.69 mmol) in pyridine (15 mL) was added drop wise over 30 min to a cooled (0° C.) solution of ethyl 3-{4-chloro-3-[(1S)-1,2-dihydroxyethyl]phenyl}propanoate (1.41 g, 5.17 mmol) in pyridine (20 mL) under N$_2$. The solution slowly warmed to rt overnight. After 16 h, 1N HCl and ethyl ether were added. The organic layer was isolated and the aqueous layer washed with ethyl ether (2×). The combined organic fractions were washed with 1N HCl, 10% aqueous Cu$_2$SO$_4$, brine, dried (Na$_2$SO$_4$), and concentrated. The crude product was purified by Biotage chromatography (0%-10% EtOAc/Hexanes) to afford 1.77 g of product as an oil (80%). $^1$H NMR (400 MHz, chloroform-d) δ ppm 7.81 (d, J=8.08 Hz, 2 H) 7.43 (d, J=2.27 Hz, 1 H) 7.36 (d, J=8.34 Hz, 2 H) 7.22 (d, J=8.08 Hz, 1 H) 7.10 (dd, J=8.21, 1.89 Hz, 1 H) 5.34 (td, J=5.62, 2.91 Hz, 1 H) 4.28 (dd, J=10.61, 2.53 Hz, 1 H) 4.14 (q, J=7.24 Hz, 2 H) 3.98 (dd, J=10.61, 8.34 Hz, 1 H) 2.93 (t, J=7.71 Hz, 2 H) 2.60 (t, J=7.83 Hz, 2 H) 2.47 (s, 3 H) 1.25 (t, J=7.07 Hz, 3 H).

(h) Ethyl 3-{4-chloro-3-[(2S)-oxiran-2-yl]phenyl}propanoate

To a solution of ethyl 3-[4-chloro-3-((1S)-1-hydroxy-2-{[(4-methylphenyl) sulfonyl]oxy}ethyl)phenyl]propanoate (1.77 g, 4.1 mmol) in absolute ethanol (12 mL) was added potassium carbonate (0.63 g, 4.6 mmol) and the reaction was stirred at rt for 3 days. The reaction was concentrated and diluted with water and extracted with EtOAc (2×). The combined organic layers were washed with H$_2$O, brine, dried (Na$_2$SO$_4$), and concentrated to afford 810 mg of product as a white solid (78%). The product was pure enough to use in the subsequent step. $^1$H NMR (400 MHz, chloroform-d) δ ppm 7.27 (d, J=8.59 Hz, 1 H) 7.07-7.10 (m, J=2.72, 2.72, 2.72, 2.72 Hz, 2 H) 4.19 (dd, J=4.04, 2.53 Hz, 1 H) 4.13 (q, J=7.07 Hz, 2 H) 3.19 (dd, J=5.68, 4.17 Hz, 1 H) 2.91 (t, J=7.71 Hz, 2 H) 2.65 (dd, J=5.56, 2.53 Hz, 1 H) 2.59 (t, J=7.58 Hz, 2 H) 1.24 (t, J=7.20 Hz, 3 H)

(i) 3-(4-Chloro-3-{(1S)-2-[(1,1-dimethyl-4-phenylbutyl)amino]-1-hydroxyethyl}phenyl) propanoic acid The title compound was prepared by substituting ethyl 3-{4-chloro-3-[(2S)-oxiran-2-yl]phenyl}propanoate for ethyl 3-{3,4-difluoro-5-[(2S)-2-oxiranyl]phenyl}propanoate

Example 28

Preparation of 3-(2,3-Dichloro-4-{(1S)-2-[(1,1-dimethyl-4-phenylbutyl)amino]-1-hydroxyethyl}phenyl)propanoic acid hydrochloride salt The title compound was prepared by substituting 4-bromo-2,3-dichlorophenol for 5-bromo-2,3-difluorophenol in step (a) of Example 1. LCMS (m/z)=438.2 [M+H].

Example 29

Preparation of 5-[2,3-Dichloro-4-((1S)-2-{[2-(2,3-dihydro-1H-inden-2-yl)-1,1-dimethylethyl]amino}-1-hydroxyethyl)phenyl]pentanoic acid hydrochloride salt The title compound was prepared by substituting 4-bromo-2,3-dichlorophenol for 5-bromo-2,3-difluorophenol and ethyl 4-pentenoate for ethyl acrylate in step (a) and [2-(2,3-dihydro-1H-inden-2-yl)-1,1-dimethylethyl]amine for (1,1-dimethyl-4-phenylbutyl)amine in step (h) of Example 1. LCMS (m/z)=478.2 [M+H].

Example 30

Preparation of 3-(3-{(1S)-2-[(1,1-Dimethyl-4-phenylbutyl)amino]-1-hydroxyethyl}-4,5-difluorophenyl)-2,2-dimethylpropanoic acid trifluoroacetate salt

(a) Ethyl 3-[3-(benzyloxy)-4,5-difluorophenyl]propanoate

A solution of DMF (21 mL), ethyl 3-(3,4-difluoro-5-hydroxyphenyl)propanoate (2.46 g, 0.0107 mol), and $K_2CO_3$ (1.92 g, 0.0139 mol) were combined at 0° C. under $N_2$. After 10 min, benzyl bromide (1.65 mL, 0.0139 mol) was added dropwise. The solution was allowed to warm to room temperature. After 16 h, $H_2O$ (50 mL), $Et_2NH$ (2 eq) and EtOAc (50 mL) were added and the organic layer isolated. The aqueous layer was washed with EtOAc (2×) and the combined organic fractions were washed with 1M HCl (2×), sat. aq. $NaHCO_3$ (2×), dried, and concentrated. The crude product was purified by flash chromatography (gradient 100% hexanes-60% EtOAc/hexanes) to afford 4.74 g of product as an oil (86%).

(b) Ethyl 3-[3-(benzyloxy)-4,5-difluorophenyl]-2,2-dimethylpropanoate

A THF (100 mL) solution of ethyl 3-[3-(benzyloxy)-4,5-difluorophenyl]propanoate (13.48 g, 0.0421 mol) under $N_2$ was cooled to −78° C. KHMDS (0.5M in toluene, 232 mL, 0.116 mol) was added dropwise over 20 minutes. The resultant solution was stirred for 45 min at −78° C. MeI (7.88 mL, 0.126 mol) was slowly added over 10 min and the solution was warmed to rt. After 16 h, saturated aq. $NH_4Cl$ was added and the product extracted with EtOAc (3×), dried ($Na_2SO_4$), concentrated and purified by flash chromatography (gradient 100% hexanes-20% EtOAc/hexanes) to afford 13.13 g of product as an oil (90%).

(c) Ethyl ethyl 3-(3,4-difluoro-5-hydroxyphenyl)-2,2-dimethyl propanoate

A solution of ethyl 3-[3-(benzyloxy)-4,5-difluorophenyl]-2,2-dimethylpropanoate (1.32 g, 0.00378 moles) and EtOH (20 mL) was degassed and flushed with $N_2$ (2×). To the solution was added 5% Pd/C (degussa type/wet 130 mg, 10% by weight) and the solution was then degassed and a $H_2$ balloon was attached. After 16 h under $H_2$, the solution was filtered through celite and concentrated to afford 860 mg of product as an oil (88%) that was used directly in the next step without purification.

(d) 3-(3-{(1S)-2-[(1,1-Dimethyl-4-phenylbutyl)amino]-1-hydroxyethyl}-4,5-difluorophenyl)-2,2-dimethylpropanoic acid The title compound was prepared by substituting ethyl ethyl 3-(3,4-difluoro-5-hydroxyphenyl)-2,2-dimethylpropanoate for ethyl 3-{3,4-difluoro-5-[(2S)-2-oxiranyl]phenyl}propanoate in Example 1 (MS ES 434.2 [M+H]$^+$).

Example 31

Preparation of 3-[3-((1S)-2-{[2-(2,3-dihydro-1H-inden-2-yl)-1,1-dimethylethyl]amino}-1-hydroxyethyl)-4,5-difluorophenyl]-2,2-dimethylpropanoic acid trifluoroacetate salt The title compound was prepared by substituting ethyl ethyl 3-(3,4-difluoro-5-hydroxyphenyl)-2,2-dimethylpropanoate for ethyl 3-{3,4-difluoro-5-[(2S)-2-oxiranyl]phenyl}propanoate and [2-(2,3-dihydro-1H-inden-2-yl)-1,1-dimethylethyl]amine for (1,1-dimethyl-4-phenylbutyl)amine in step (h) of Example 1 (MS ES 446.2 [M+H]$^+$).

Example 32

Preparation of 3-[3-((1S)-2-{[2-(3-chloro-4-fluorophenyl)-1,1-dimethylethyl]amino}-1-hydroxyethyl)-4,5-difluorophenyl]propanoic acid hydrochloride salt The title compound was prepared by substituting [2-(4-chloro-3-fluorophenyl)-1,1-dimethylethyl]amine for (1,1-dimethyl-4-phenylbutyl)amine in step (h) of Example 1. (MS ES 430/432 [M+H]$^+$).

Example 33

Preparation of 3-[3-((1S)-2-{[1,1-dimethyl-2-(3-thienyl)ethyl]amino}-1-hydroxyethyl)-4,5-difluorophenyl]propanoic acid hydrochloride salt The title compound was prepared by substituting [1,1-dimethyl-2-(3-thienyl)ethyl]amine for (1,1-dimethyl-4-phenylbutyl)amine in step (h) of Example 1. (LC-MSD Trap SL 384 [M+H]$^+$).

Example 34

Preparation of 3-{3,4-difluoro-5-[(1S)-1-hydroxy-2-({1-methyl-1-[4-(methyloxy)phenyl]ethyl}amino)ethyl]phenyl}propanoic acid hydrochloride salt The title compound was prepared by substituting 2-[4-(methyloxy)phenyl]-2-propanamine for (1,1-dimethyl-4-phenylbutyl)amine in step (h) of Example 1. (LC-MSD Trap SL 394 [M+H]$^+$).

Example 35

Preparation of 3-[3-((1S)-2-{[2-(2,3-dihydro-1H-inden-2-yl)-1,1-dimethylethyl]amino}-1-hydroxyethyl)-4-fluorophenyl]propanoic acid hydrochloride salt The title compound was prepared by substituting 5-bromo-2-fluorophenol for 5-bromo-2,3-difluorophenol in step (a) of Example 1. (LC-MSD Trap SL 388 [M+H]$^+$).

Example 36

Preparation of 3-[3-((1S)-2-{[2-(2,3-dihydro-1H-inden-2-yl)-1,1-dimethylethyl]amino}-1-hydroxyethyl)-4-fluorophenyl]propanoic acid hydrochloride salt The title compound was prepared by substituting 5-bromo-2-fluorophenol for 5-bromo-2,3-difluorophenol in step (a) and [2-(2,3-dihydro-1H-inden-2-yl)-1,1-dimethylethyl]amine for (1,1-dimethyl-4-phenylbutyl)amine in step (h) of Example 1. (LC-MSD Trap SL 400 [M+H]$^+$).

Example 37

Preparation of 5-(3-{(1S)-2-[(1,1-dimethyl-4-phenylbutyl)amino]-1-hydroxyethyl}-4-fluorophenyl)pentanoic acid hydrochloride salt The title compound was prepared by substituting 5-bromo-2-fluorophenol for 5-bromo-2,3-difluorophenol and ethyl pentenoate for ethyl acrylate in step (a) of Example 1. (MS ES 416 [M+H]$^+$).

Example 38

Preparation of 5-[3-((1S)-2-{[2-(2,3-dihydro-1H-inden-2-yl)-1,1-dimethylethyl]amino}-1-hydroxyethyl)-4-fluorophenyl]pentanoic acid hydrochloride salt The title compound was prepared by substituting 5-bromo-2-fluorophenol for 5-bromo-2,3-difluorophenol and ethyl pentenoate for ethyl acrylate in step (a) and [2-(2,3-dihydro-1H-inden-2-yl)-1,1-dimethylethyl]amine for (1,1-dimethyl-4-phenylbutyl)amine in step (h) of Example 1. (MS ES 428 [M+H]$^+$).

Example 39

Preparation of 4-(3-{(1S)-2-[(1,1-dimethyl-4-phenylbutyl)amino]-1-hydroxyethyl}-4-fluorophenyl)butanoic acid hydrochloride salt The title compound was prepared by substituting 5-bromo-2-fluorophenol for 5-bromo-2,3-difluorophenol and ethyl butenoate for ethyl acrylate in step (a) of Example 1. (MS ES 402 [M+H]$^+$).

Example 40

Preparation of 3-(2-{(1S)-2-[(1,1-dimethyl-4-phenylbutyl)amino]-1-hydroxyethyl}-3,4-difluorophenyl)propanoic acid hydrochloride salt (a) 2,3-difluoro-6-(hydroxymethyl)phenol To a solution of 3,4-difluoro-2-hydroxy benzoic acid (3.2 g 18.39 mmol) in THF (20 mL) was added BH$_3$.Me$_2$S (7 mL 73.56 mmol) drop wise, over a period of 20 min. at RT. The reaction mixture was stirred at RT for 3 h and monitored by TLC. Methanol (20 mL) was added and the solvent was removed under vacuum. The crude compound was purified by column chromatography over silica gel using a mixture of ethyl acetate and hexane (20:80) as eluent to give the alcohol (2.7 g, 91% yield) MS: m/z 159 (M+1).

(b) 3,4-difluoro-2-hydroxybenzaldehyde

To a stirred solution of 2,3-difluoro-6-(hydroxylmethyl)phenol (2.5 g, 15.62 mmol) in dichloromethane (20 mL) was added a suspension of DDQ (5.32 g, 23.43 mmol) in dichloromethane (10 mL) at −5-0° C. The reaction mixture was stirred at room temperature overnight. TLC indicated absence of starting material. Reaction mixture was filtered through a bed of celite and the filtrate was concentrated in vacuum. The crude compound was purified by column chromatography over silica gel using dichloromethane (100%) as eluent to give the aldehyde derivative (2 g, 83% yield) MS: m/z 157 (M+1).

(c) ethyl (2E)-3-(3,4-difluoro-2-hydroxyphenyl)-2-propenoate (Carbethoxymethylene) triphenylphosphorane (10.90 g, 31.32 mmol) was added to the solution of 3,4-difluoro-2-hydroxy benzaldehyde (3.3 g, 20.88 mmol) in toluene (15 mL) at room temperature. The reaction mixture was stirred at RT for 3 h under nitrogen, and the reaction was monitored by TLC. The solvent was removed under vacuum and the residue was purified by column chromatography over silica gel using a mixture of ethyl acetate and hexane (0-20%) to give the olefin (4 g, 85% yield) as a light yellow solid. MS: m/z 229 (M+1).

(d) ethyl 3-(3,4-difluoro-2-hydroxyphenyl)-2-propanoate

To a solution of the olefin (2 g, 8.77 mmol) in ethanol (30 mL) was added Pd/C (0.2 g, 10% Pd/C). The reaction mixture was stirred under hydrogen atmosphere (60 psi) for 2 h and monitored by TLC. The mixture was filtered though a pad of celite and washed with additional amount of methanol and concentrated to get the desired product (2 g, 98% yield) MS: m/z 231 (M+1).

(e) 3-(2-{(1S)-2-[(1,1-dimethyl-4-phenylbutyl)amino]-1-hydroxyethyl}-3,4-difluorophenyl)propanoic acid The title compound was prepared by substituting ethyl (2E)-3-(3,4-difluoro-2-hydroxyphenyl)-2-propanoate for Ethyl 3-(3,4-difluoro-5-hydroxyphenyl)propanoate in step (b) of Example 1 (LC-MSD Trap SL 432 [M+H]$^+$).

Example 41

Preparation of 5-(4-{(1S)-2-[(1,1-dimethyl-4-phenyl butyl)amino]-1-hydroxyethyl}-2,3-difluorophenyl) pentanoic acid hydrochloride salt The title compound was prepared by substituting 4-bromo-2,3-difluorophenol for 5-bromo-2,3-difluorophenol and ethyl pentenoate for ethyl acrylate in step (a) of Example 1. (MS ES 434 [M+H]$^+$).

Example 42

Preparation of 5-[4-((1S)-2-{[2-(2,3-dihydro-1H-inden-2-yl)-1,1-dimethylethyl]amino}-1-hydroxyethyl)-2,3-difluorophenyl]pentanoic acid hydrochloride salt The title compound was prepared by substituting 4-bromo-2,3-difluorophenol for 5-bromo-2,3-difluorophenol and ethyl pentenoate for ethyl acrylate in step (a) and [2-(2,3-dihydro-1H-inden-2-yl)-1,1-dimethylethyl]amine for (1,1-dimethyl-4-phenylbutyl)amine in step (h) of Example 1. (MS ES 446 [M+H]$^+$).

The above description fully discloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:

1. A compound according to Formula (I):

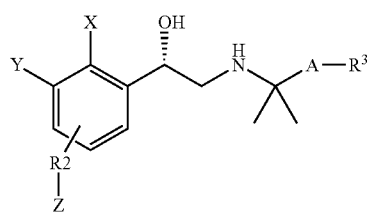

(I)

wherein:
X is halogen;
Y is hydrogen or halogen;
Z is —CO(O)H or —C(O)OC$_{1-5}$alkyl;
R2 is C$_{1-5}$alkyl;
R3 is phenyl, thienyl, naphthyl or dihydroindenyl, wherein the thienyl and phenyl moieties are optionally substituted, independently, once or twice, by halogen, C$_{1-5}$alkyl, C$_{1-5}$alkoxy or C$_{1-5}$alkylthio; and
A is a covalent bond or C$_{1-5}$alkyl;
or a pharmaceutically acceptable salt thereof.

2. The compound according to claim 1 wherein X is F.
3. The compound according to claim 1 wherein Y is F.
4. The compound according to claim 1 wherein R2 is ethyl.
5. The compound according to claim 1 wherein R3 is 2,3-dihydro-1H-inden-2-yl.
6. The compound according to claim 1 wherein R3 is phenyl.
7. The compound according to claim 1 wherein R3 is phenyl, substituted once by a substituent selected from the group consisting of halogen, C$_{1-5}$alkyl, C$_{1-5}$alkoxy and C$_{1-5}$alkylthio.
8. The compound according to claim 1 wherein R3 is phenyl, substituted independently, twice, by C$_{1-5}$alkyl or halogen.
9. The compound according to claim 1 wherein:
X is F;
Y is F;
Z is —CO(O)H;
R2 is ethyl;
R3 is phenyl; and
A is propyl;
or a pharmaceutically acceptable salt thereof.
10. The compound according to claim 1 selected from the group consisting of:
3-(3-{(1S)$_2$-[(1,1-dimethyl-4-phenylbutyl)amino]-1-hydroxyethyl}-4,5-difluorophenyl)propanoic acid;
ethyl 3-(3-{(1S)-2-[(1,1-dimethyl-4-phenylbutyl)amino]-1-hydroxyethyl}-4,5-difluorophenyl)propanoate;
ethyl 3-[3-((1S)-2-{[2-(2,3-dihydro-1H-inden-2-yl)-1,1-dimethylethyl]amino}-1-hydroxyethyl)-4,5-difluorophenyl]propanoate;
3-[3-((1S)-2-{[2-(2,3-dihydro-1H-inden-2-yl)-1,1-dimethylethyl]amino}-1-hydroxyethyl)-4,5-difluorophenyl]propanoic acid;
5-(3-{(1S)-2-[(1,1-dimethyl-4-phenylbutyl)amino]-1-hydroxyethyl}-4,5-difluorophenyl)pentanoic acid;
5-[3-((1S)-2-{[2-(2,3-dihydro-1H-inden-2-yl)-1,1-dimethylethyl]amino}-1-hydroxyethyl)-4,5-difluorophenyl]pentanoic acid;
4-(3-{(1S)-2-[(1,1-dimethyl-4-phenylbutyl)amino]-1-hydroxyethyl}-4,5-difluorophenyl)butanoic acid;
4-[3-((1S)-2-{[2-(2,3-dihydro-1H-inden-2-yl)-1,1-dimethylethyl]amino}-1-hydroxyethyl)-4,5-difluorophenyl]butanoic acid;
3-(3-{(1S)-2-[(1,1-dimethyl-5-phenylpentyl)amino]-1-hydroxyethyl}-4,5-difluorophenyl)propanoic acid;
3-[3-((1S)-2-{[2-(4-chloro-3-fluorophenyl)-1,1-dimethylethyl]amino}-1-hydroxyethyl)-4,5-difluorophenyl]propanoic acid;
3-{3-[(1S)-2-({1,1-dimethyl-2-[4-(methyloxy)phenyl]ethyl}amino)-1-hydroxyethyl]-4,5-difluorophenyl}propanoic acid;
3-[3-((1S)-2-{[1,1-dimethyl-2-(2-naphthalenyl)ethyl]amino}-1-hydroxyethyl)-4,5-difluorophenyl]propanoic acid;
3-(3-{(1S)-2-[(1,1-dimethyl-2-phenylethyl)amino]-1-hydroxyethyl}-4,5-difluorophenyl)propanoic acid;
3-(3,4-difluoro-5-{(1S)-1-hydroxy-2-[(1-methyl-1-phenylethyl)amino]ethyl}phenyl)propanoic acid;
3-[3-((1S)-2-{[2-(4-chloro-2-fluorophenyl)-1,1-dimethylethyl]amino}-1-hydroxyethyl)-4,5-difluorophenyl]propanoic acid;
3-[3-((1S)-2-{[1,1-dimethyl-2-(5-methyl-2-thienyl)ethyl]amino}-1-hydroxyethyl)-4,5-difluorophenyl]propanoic acid;

3-{3-[(1S)-2-({1,1-dimethyl-3-[4-(methyloxy)phenyl]propyl}amino)-1-hydroxyethyl]-4,5-difluorophenyl}propanoic acid;

3-[3,4-difluoro-5-((1S)-2-{[2-(3-fluoro-4-methylphenyl)-1,1-dimethylethyl]amino}-1-hydroxyethyl)phenyl]propanoic acid;

3-{3-[(1S)-2-({1,1-dimethyl-2-[4-(methylthio)phenyl]ethyl}amino)-1-hydroxyethyl]-4,5-difluorophenyl}propanoic acid;

3-{3-[(1S)-2-({2-[4-(1,1-dimethylethyl)phenyl]-1,1-dimethylethyl}amino)-1-hydroxyethyl]-4,5-difluorophenyl}propanoic acid;

3-[3-((1S)-2-{[1,1-dimethyl-2-(2-thienyl)ethyl]amino}-1-hydroxyethyl)-4,5-difluorophenyl]propanoic acid;

3-(3-{(1S)-2-[(1,1-dimethyl-3-phenylpropyl)amino]-1-hydroxyethyl}-4,5-difluorophenyl)propanoic acid;

3-[3-((1S)-2-{[2-(4-bromophenyl)-1,1-dimethylethyl]amino}-1-hydroxyethyl)-4,5-difluorophenyl]propanoic acid;

3-[3-((1S)-2-{[2-(5-chloro-2-thienyl)-1,1-dimethylethyl]amino}-1-hydroxyethyl)-4,5-difluorophenyl]propanoic acid;

2-(3-{(1S)-2-[(1,1-dimethyl-4-phenylbutyl)amino]-1-hydroxyethyl}-4,5-difluorophenyl)-2-methylpropanoic acid;

2-[3-((1S)-2-{[2-(2,3-dihydro-1H-inden-2-yl)-1,1-dimethylethyl]amino}-1-hydroxyethyl)-4,5-difluorophenyl]-2-methylpropanoic acid;

3-(4-chloro-3-{(1S)-2-[(1,1-dimethyl-4-phenylbutyl)amino]-1-hydroxyethyl}phenyl)propanoic acid;

3-(2,3-dichloro-4-{(1S)-2-[(1,1-dimethyl-4-phenylbutyl)amino]-1-hydroxyethyl}phenyl)propanoic acid;

5-[2,3-dichloro-4-((1S)-2-{[2-(2,3-dihydro-1H-inden-2-yl)-1,1-dimethylethyl]amino}-1-hydroxyethyl)phenyl]pentanoic acid;

3-(3-{(1S)-2-[(1,1-dimethyl-4-phenylbutyl)amino]-1-hydroxyethyl}-4,5-difluorophenyl)-2,2-dimethylpropanoic acid; and 3-[3-((1S)-2-{[2-(2,3-dihydro-1H-inden-2-yl)-1,1-dimethylethyl]amino}-1-hydroxyethyl)-4,5-difluorophenyl]-2,2-dimethylpropanoic acid;

or a pharmaceutically acceptable salt thereof.

11. The compound according to claim 10 wherein the compound is 3-(3-{(1S)$_2$-[(1,1-dimethyl-4-phenylbutyl)amino]-1-hydroxyethyl}-4,5-difluorophenyl)propanoic acid.

12. A pharmaceutical composition comprising the compound according to claim 1 and a pharmaceutically acceptable carrier or diluent.

13. A method of treating a disease or disorder characterized by an abnormal bone or mineral homeostasis, which comprises inhibiting a calcium receptor by administering to a subject in need of treatment thereof an effective amount of the compound according to claim 1.

14. The method according to claim 13 wherein the abnormal bone or mineral homeostasis disease or disorder is selected from the group consisting of osteosarcoma, periodontal disease, fracture healing, osteoarthritis, rheumatoid arthritis, Paget's disease, hypoparathyroidism, humoral hypercalcemia associated with malignancy and fracture healing, and osteoporosis.

15. The method according to claim 14 wherein the bone or mineral disease or disorder is osteoporosis.

16. A method of increasing serum parathyroid levels by inhibiting a calcium receptor which comprises administering to a subject in need of treatment an effective amount of the compound according to claim 1.

17. The method according to claim 13 wherein the compound according to Formula (I) is co-administered with an anti-resorptive agent.

* * * * *